(12) United States Patent
Alster et al.

(10) Patent No.: US 7,275,830 B2
(45) Date of Patent: Oct. 2, 2007

(54) METHODS DEVICES AND SYSTEMS FOR DETECTING EYE DISEASE

(75) Inventors: Yair Alster, Tel Aviv (IL); Omer Refaeli, Givatayim (IL); Barak Azmon, Tel Aviv (IL)

(73) Assignee: Notal Vision Inc., Wilmington New Castle, DE (US)

( * ) Notice: Subject to any disclaimer, the term of this patent is extended or adjusted under 35 U.S.C. 154(b) by 826 days.

(21) Appl. No.: 10/398,375

(22) PCT Filed: Oct. 7, 2001

(86) PCT No.: PCT/IL01/00933

§ 371 (c)(1),
(2), (4) Date: Oct. 20, 2003

(87) PCT Pub. No.: WO02/28266

PCT Pub. Date: Apr. 11, 2002

(65) Prior Publication Data

US 2004/0075814 A1    Apr. 22, 2004

(30) Foreign Application Priority Data

Oct. 6, 2000   (IL) .................................... 138926

(51) Int. Cl.
*A61B 3/02*   (2006.01)
(52) U.S. Cl. ...................... 351/223; 351/224; 351/237; 351/246
(58) Field of Classification Search ........ 351/222–224, 351/237, 239–243, 246
See application file for complete search history.

(56) References Cited

U.S. PATENT DOCUMENTS

| 4,349,250 | A | 9/1982 | Gelius |
| 4,798,456 | A | 1/1989 | Enoch et al. |
| 4,822,162 | A | 4/1989 | Richardson et al. |
| 4,995,717 | A | 2/1991 | Damato |
| 5,412,561 | A | 5/1995 | Rosenshein et al. |
| 5,463,431 | A | 10/1995 | Suzuki et al. |
| 5,506,633 | A | 4/1996 | Sperling |
| 5,539,482 | A | 7/1996 | James et al. |

(Continued)

OTHER PUBLICATIONS

Jay M. Enoch et al., "Hyperacuity Perrimetry: Assessment of Macular Function Through Ocular Opacities", Arch Ophthalmol, vol. 112, Aug. 1984, pp. 1164-1168.

(Continued)

*Primary Examiner*—Huy Mai
(74) *Attorney, Agent, or Firm*—Daniel J. Swirsky; AlphaPatent Associates Ltd.

(57) ABSTRACT

Methods and systems for performing an eye test and for detecting eye disease. A test pattern is presented to an individual. The individual fixates an eye on a fixation target. The test pattern is then hidden and a second test pattern is displayed at a different location. The individual then compares the perceived second test pattern with a pre-defined reference pattern. These steps are repeated several times, while varying the location of presentation of the patterns. Alternatively, the individual fixates on a presented fixation target. A test pattern is presented to the patient and then disappears. The individual compares the perceived pattern, with a pre-defined reference pattern. These steps are repeated while changing the location of presentation of the test pattern. It may then be determined whether the individual has an eye disease based on the comparisons.

254 Claims, 12 Drawing Sheets

U.S. PATENT DOCUMENTS

| | | | |
|---|---|---|---|
| 5,565,949 | A | 10/1996 | Kasha, Jr. |
| 5,589,897 | A | 12/1996 | Sinclair et al. |
| 5,864,384 | A | 1/1999 | McClure et al. |
| 5,883,692 | A | 3/1999 | Agonis et al. |
| 5,892,570 | A | 4/1999 | Stevens |
| 5,946,075 | A | 8/1999 | Horn |
| 6,027,217 | A | 2/2000 | McClure et al. |
| 6,033,076 | A | 3/2000 | Braeuning et al. |
| 6,520,640 | B1 | 2/2003 | Binnun |
| 6,527,391 | B1 | 3/2003 | Heijl et al. |
| 6,578,966 | B2 | 6/2003 | Fink et al. |
| 6,585,376 | B1 | 7/2003 | Matsumoto |
| 6,656,131 | B2 * | 12/2003 | Alster et al. ............ 600/558 |
| 6,688,746 | B2 | 2/2004 | Malov |
| 6,742,894 | B2 | 6/2004 | Stewart |
| 6,920,358 | B2 * | 7/2005 | Greenberg et al. ............ 607/54 |
| 2002/0042580 | A1 | 4/2002 | Alster et al. |

OTHER PUBLICATIONS

Michael Wall and Alfredo A. Sadun, "Threshold Amsler Grid Testinng: Cross-Polarizing Lenses Enhance Yield", Arch Ophthalmol, vol. 104, Apr. 1986, pp. 520-523.

Stuart L. Fina and the Macular Photocoagulation Study Group, "Early Detection of Extrafoveal Neovascular Membranes by Daily Central Field Evaluation", Wilmer Ophthalmological Institute, John Hopkins University, Johns Hopkins University, presented at meeting which took place between Oct. 30-Nov. 3, 1984, pp. 603-609.

Vasudevan Lakshminarayanan et al., "Quantifications of Metamorphopsia Using Hyperacuity Techniques", Optometry and Vision Science, vol. 68, No. 12,, 1991, pp. 942-945.

Michael J. Tolentino et al., "Visual Field Deficits in Early Age-Related Macular Degeneration", Vision Res., vol. 34, No. 3, pp. 409-413, 1994.

Reginald G. Ariyasu et al., "Sensitivity, Specificity and Predicitive Values of Screening Tests for Eye Conditions in a Clinic-Based Population", Ophthamology, vol. 103, No. 11, Nov. 1996, pp. 1751-1760.

Michael L. Slavin, "The Use of the Red Amsler Grid and Red-Green Lenses in Detecting Spurious Paracentral Visual Field Defects", American Journal of Opthalmology, vol. 103, No. 3, Part 1, Mar. 1987, pp. 338-339.

Michael Wall and Donald R. May, "Threshold Amsler Grid Testing in Maculopathies", Presented at the American Academy of Opthalmolgy Annual Meeting, New Orleans, Nov 1986, pp. 1126-1133.

* cited by examiner

METHODS DEVICES AND SYSTEMS FOR DETECTING EYE DISEASE

CROSS-REFERENCE TO RELATED APPLICATIONS

This application is a National Phase Application of International Patent Application Number PCT/IL01/00933, filed Oct. 7, 2001, which is incorporated herein by reference in its entirety for all purposes.

FIELD OF THE INVENTION

This invention relates to systems, devices, and methods for administering eye tests and for detecting eye disease.

BACKGROUND OF THE INVENTION

Age-related macular degeneration (AMD) is the leading cause of blindness among people over the age of 50 in the western world. It is a bilateral, although asymmetric disease, and comes in two forms. Dry or non-neovascular AMD is the more common and milder form of AMD, accounting for 85-90% of all AMD. The key identifier for dry AMD is small, round, white-yellow lesions (also known as Drusen) in the macula. Vision loss associated with dry AMD is far less dramatic than in the case of wet AMD. There is currently no treatment available for dry AMD. It is estimated that as many as 14 million people suffer from dry AMD in the United States alone.

Wet AMD is less prevalent than the dry form, accounting for about 10-15% of AMD cases. The term "wet" denotes choroidal neovascularization (CNV), in which abnormal blood vessels develop beneath the retinal pigment epithelium (RPE) layer of the retina. Wet AMD is characterized by the development of choroidal angiogenesis which causes severe, and potentially rapid, visual deterioration. The visual distortion typically consists of perceiving straight lines as curved due to deformation of the retina in a region overlying the choroidal angiogenesis. The wet form of AMD accounts for about 60% of all cases of adult blindness in the United States. In the U.S. alone there are 200,000 new cases of wet AMD every year and a total of 1.7 million blind people from AMD.

Treatment modalities for wet AMD may include conventional treatments such as laser photocoagulation and newer treatment modalities such as Photodynamic therapy (PDT). Experimental treatments that are under current investigation include feeder vessel coagulation and trans-pupillary thermotherapy (TTT). All these proven or experimental therapies may halt or slow progression of the disease only if detected at an early stage and will not reverse existing retinal damage. Therefore, early detection is crucial to prevent severe visual loss.

Since approximately 12% of dry AMD cases develop wet AMD and subsequent blindness within 10 years, a patient diagnosed with dry AMD must be routinely examined by an ophthalmologist once or twice a year, depending on the severity of his condition. The patient is usually also given a so-called "Amsler grid" for weekly self-examination at home for symptoms of wet AMD. The patient is advised to consult an ophthalmologist immediately in the event that symptoms are noticed. The Amsler grid and its modifications (such as the "threshold Amsler" or the "red Amsler") have been shown to be poor detectors of early changes associated with wet AMD for several reasons. One reason is the phenomenon of "filling-in" whereby the brain fills in missing parts in the pattern or corrects defects or distortions in the pattern. The subject thus fails to perceive a distorted pattern as being distorted. Another problem with the Amsler grid is the inability of patients to adequately fixate their vision on a fixed point while taking the test. The Amsler test also suffers from low compliance stemming from the non-interactive nature of the test.

The degree of visual deterioration is a function of the size of the lesion and its proximity to the fovea at the time of diagnosis. Although most lesions probably start outside the foveal area, 70% are already foveal and large (>1500 microns) at the time of diagnosis. It is therefore crucial to identify the lesions at the earliest possible stage, while they are still small and have not reached the fovea. It is known that 70% of lesions diagnosed as treatable become untreatable within less than three months, which indicates that the progression of the disease is relatively rapid. As many as 70-80% of patients with wet AMD are already ineligible for treatment when they first consult their ophthalmologist because the disease has progressed considerably. This is due to the poor validity of existing self-assessment methods for detecting an AMD-related lesion at an early stage, and the time lapsed between noticing the symptoms and seeing an ophthalmologist.

A reliable method for diagnosing wet AMD at the earliest possible stage, in conjunction with a referral system aimed at lowering the incidence of visual deterioration in this devastating disease, are imperative. If detected early, laser therapy to destroy the abnormal blood vessels may prevent additional vision loss. It is therefore crucial to detect the transition from dry to wet AMD as early as possible.

SUMMARY OF THE INVENTION

The present invention provides an eye test for detecting retinal lesions such as those associated with AMD, diabetes, or the like. The method involves showing a subject a first test pattern displayed on a surface. The test pattern may be, for example, one or more straight lines or one or more straight segmented lines, but other types of test patterns may also be used. The subject then fixates his vision on a fixation target. The fixation target may be a part or a component of the test pattern or may be any other type of suitable pattern presented near, or at or in the vicinity of the test pattern. The first test pattern may be then hidden (or made to disappear) and a second test pattern is displayed at a different location on the surface. The second test pattern may be substantially identical to the first pattern, or the two patterns may be different. For example, the second test pattern may have one or more component or region that is modified or mis-aligned of blurred or spatially shifted in a way that makes the test pattern different than a predefined reference pattern. Test pattern which are different than the predefined reference pattern are referred to as artificially modified or artificially distorted test patterns. The subject is then asked to compare the second pattern and the predefined reference pattern.

In accordance with one embodiment of the invention, the predefined reference pattern may be the first test pattern shown to the subject. In accordance with another embodiment of the invention, the predefined reference pattern may be a virtual pattern mentally conceived by the subject based on the visual experience of the subject. For example, in accordance with one possible non-limiting example of the invention, the subject may be told in a training session that he is going to be presented with test patterns which may or may not differ from a straight segmented line and that he is to indicted which if any of the segments of the presented test patterns appear to be different than a straight segmented line. In accordance with is embodiment, the subject may conceive an idea of what the reference pattern is before he is shown any test patterns.

If the second test pattern and the predefined reference pattern were identical, but the subject has perceived them to be different, this may be indicative of a lesion of the retina (or another eye disease or abnormality). The subject indicates a region in the second test pattern that appears to him to be different or to change in appearance or position as compared to the corresponding region in the predefined reference pattern. The location of the lesion on the retina is determined from the location of the region in the second test pattern on the surface relative to the fixation target where the subject's vision was initially fixated. If the second test pattern and the predefined reference pattern were not identical, but the subject reports that the two patterns were identical, this may indicate that he is not responding reliably to the test.

In accordance with an embodiment of the present invention, a quantitative test reliability criterion may be established. For example, if the subject does not correctly identify the location of the modification or distortion in a predefined percentage of all the artificially modified or artificially distorted test patterns, the test results may be declared or classified as unreliable. Various different quantitative criteria may be used to determine the correctness of localization of the modification or distortion by the subject.

Thus, the second test pattern may be obtained by modifying the predefined reference pattern to simulate the predefined reference pattern as perceived by a person with a retinal lesion or an eye disease. For example, the second test pattern may be obtained from the reference pattern by displacing one or more components of the reference pattern relative to the remaining components, removing one or more components of the predefined pattern, blurring a component, or altering an optical property of a component of the predefined pattern, such, for example as color or brightness of the component. Such artificially modified or artificially distorted test patterns may also be used to demonstrate to subjects various types of visual disturbances associated with retinal lesions.

Since the subject will spontaneously shift his vision from the fixation target to the second pattern within about 200 milliseconds after it appears, the subject may additionally or alternatively be asked to indicate whether any motion occurred of part of the second pattern relative to other parts of the second pattern as he shifted his vision, and if so, where in the second pattern the motion occurred. For example, a segment of a line that appears curved when in the periphery of the subject's field of vision may appear to straighten as the subject shifts his vision and brings the pattern into the center of his field of vision. This apparent movement at the particular location in the pattern as the subject shifts his vision is indicative of a retinal abnormality in the corresponding region of the retina.

The test is repeated several times, each time presenting the second pattern in a different region in the subject's field of view. This allows a retinal abnormality or lesion to be mapped on the retina.

In a preferred embodiment, the method is performed by displaying the patterns on a display device such as a computer monitor, television, or stand-alone device. In this embodiment, the subject can be made to fixate his vision on a point of the screen of the display device which is used by having him bring a cursor to the point on the screen using any computer input device such as a computer mouse, a keyboard, joystick or touch-screen. This causes the first test pattern to disappear from the screen and the second test pattern to appear on the screen. The test patterns may consist of one or more broken lines consisting of a plurality of segments. The subject indicates a segment in the second pattern that appears different to him than the corresponding segment in the first pattern by bringing the cursor to the point and clicking the mouse. For example, if the first and second test patterns are broken or segmented lines, and the subject may perceive the first test pattern as being straight, but may perceive the second test pattern as having one or more unaligned segments, the subject would click the unaligned segments with the mouse.

The results of the test may be typically transmitted in real time over a communications network to a processor or a computer. The network may be a computer network such as a local area network (LAN), a wide area network (WAN), a private area network (PAN). The network may also be a telephone network based on the public service telephone network (PSTN) and using a modems and TCP/IP protocols such as the internet, or any other such network using any suitable communication protocols known in the art. The processor or computer may analyze the subject's responses and may generate a diagnosis of the subject's condition. The diagnosis and a recommendation for follow-up or referral for prompt examination may then be transmitted over the communication system or network to the subject and to his health care provider. The subject's compliance may be monitored regularly by the processor or computer by storing in a memory the dates that the subject is to perform the test. Failure to perform the test on schedule may result in a reminder being sent to the subject over the communication network or by telephone or by any other suitable messaging means to perform the test. A notice may also be sent to the health care provider.

In accordance with another embodiment of the present invention, the test may be applied by explaining to the subject that he is about to be presented with test patterns which may be identical to or may differ from a predetermined reference pattern. For example, the subject may be told that the reference pattern is a straight segmented line, to enable the subject to mentally conceive how the reference pattern should look like.

The test may then be performed by presenting a fixation target at a fixed position on the screen of the display device used. The subject may, for example, then fixate a tested eye on the fixation target and may indicate fixation by bringing a cursor to point at the fixation target and clicking a button on a mouse to indicate fixation. Other fixation methods may also be used. After the subject indicated fixation, a test pattern may be briefly presented to the subject on the screen at a location different than the location of the fixation target. The presented test pattern may be, for example, a straight segmented line, or an artificially distorted or modified segmented line as disclosed hereinabove. The patient may or may not perceive a change or distortion or other modification in the perceived image of the presented test pattern as compared to a predefined reference pattern The subject may then mark the part or parts or regions on the presented at which a difference or modification was observed as compared to the predefined reference pattern. Artificially distorted or artificially modified test patterns may or may not be used as disclosed hereinabove, If such artificially modified patterns are used they may be used as test reliability criteria as disclosed hereinabove. The results of the tests are stored as the positions along the presented test patterns at which differences were perceived by the patient. The results may then be analyzed or processed according to various different diagnostic methods applying selected diagnostic criteria to find if the patient is diagnosed positive or negative. Positive diagnosis may result in the patient being referred to an ophtalmologist or other eye expert to test whether a retinal lesion is present or whether there is any worsening in the patient's condition such as the beginning of retinal lesions due to wet AMD or the like.

BRIEF DESCRIPTION OF THE DRAWINGS

The invention is herein described, by way of example only, with reference to the accompanying drawings, in which like components are designated by like reference numerals, wherein.

DETAILED DESCRIPTION OF THE INVENTION

The following terms are used throughout the application:

| Term | Definition |
| --- | --- |
| AMD | Age-related macular degeneration |
| RPE | Retinal pigment epithelium |
| TTT | Trans-pupilary Thermotherapy |
| PDT | Photodynamic Therapy |

-continued

| Term | Definition |
| --- | --- |
| CNV | Choroidal Neovascularization |
| LAN | Local area network |
| WAN | Wide area network |
| PAN | Private area network |
| PSTN | Public service telephone network |
| SLO | Scanning Laser Ophtalmoscope |
| HRC | High risk characteristics |
| GA | Geographic atrophy |
| MOPT | Macular computerized psychphysical test |

It is noted that the test or tests for eye disease of the present invention t disclosed hereinbelow may also be generally referred to as the Macular computerized psychphysical test (MCPT) hereinafter.

Figure 1:
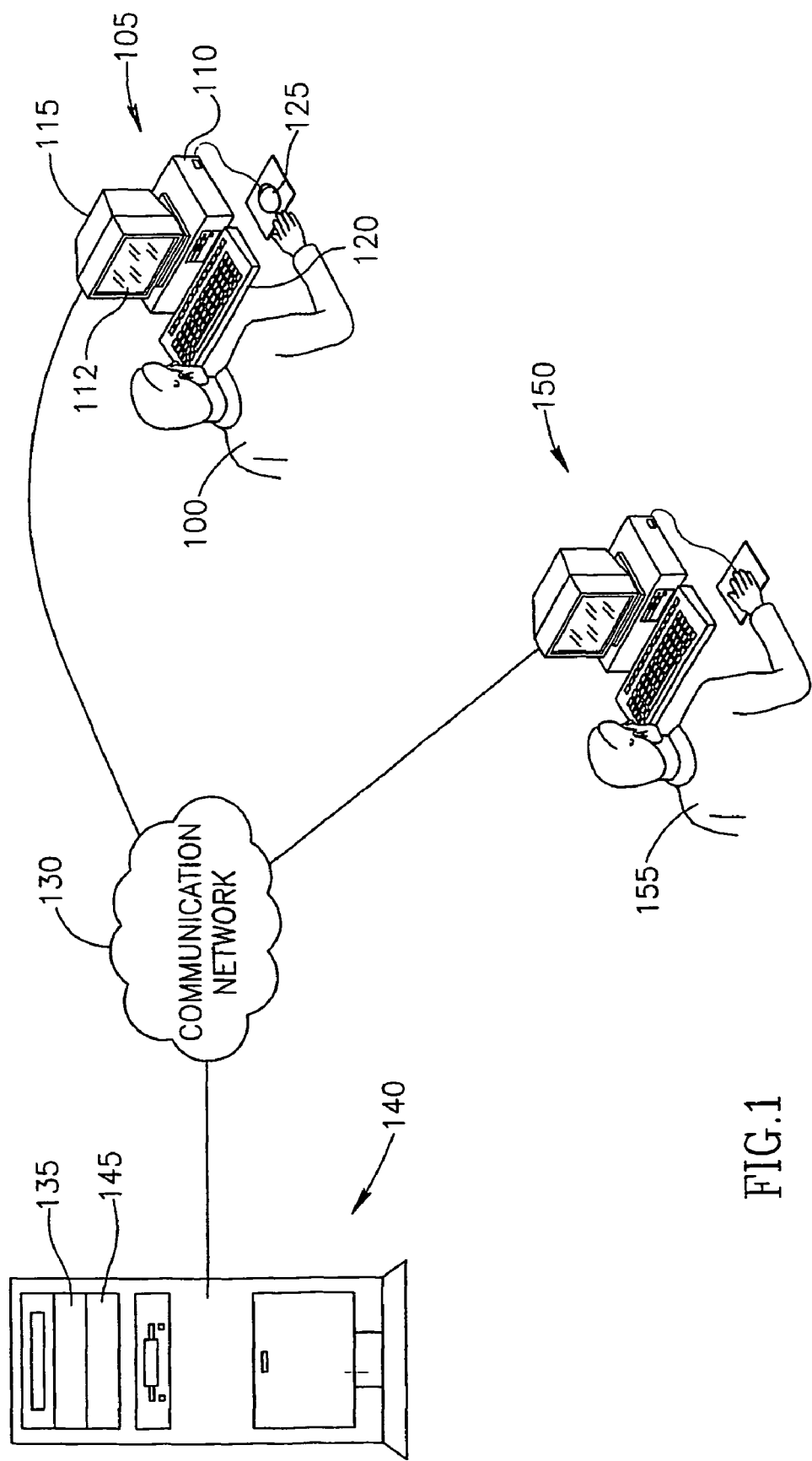
FIG. 1 is a schematic diagram illustrating a system for carrying out an eye test to detect an eye disease according to one embodiment of the invention.

FIG. 1 is a schematic diagram illustrating a system for carrying out an eye test to detect an eye disease according to one embodiment of the invention. A subject 100 performs an eye test using a computer system 105. The computer system 105 may comprise a computer 110, a display device 115 having a screen 112 and one or more computer input devices such as a keyboard 120 or a computer mouse 125. The computer system 105 may communicate over a communication network schematically indicated by the cloud labeled 130. The network 130 may be, for example, the Internet, a local area network (LAN), a wide area network (WAN), an Intranet, a private area network (PAN), virtual networks implemented over the Internet, other private and/or commercial communication networks, or any other suitable type of communication network known in the art.

A processor 135 in a network server 140 stores data relating to execution of an eye test to be performed by the subject 100 to be described in detail below. The eye test is communicated from the server 140 to the subject's computer 110 over the network 130. The subject 100 inputs responses to the eye test using one or more of the computer input devices such as the keyboard 120 or the mouse 125. The subject's responses are communicated over the network 130 to the processor 135, and stored in the memory 145. The processor 135 is configured to analyze the subject's response, to make a diagnosis of the subject's conditions and to recommend future follow-up or recommend prompt examination, all in real time, for the subject. The diagnosis and recommendation may be communicated over the network 130 to the subject's computer system 105 and/or to a terminal 150 of a health care provider 155. The processor 135 is also configured to store in the memory 145 dates on which the subject is to perform an eye test executed by the processor 135. If, for example, the subject 100 has been instructed by the health and provider 155 to perform the test once per week, the processor 135 may send a message over the communication network 130 when 10 days have elapsed since the last time he took the test, informing the subject of his failure to take the test as instructed. A similar message may be sent to the health care provider 155. A responsible individual may be designated, in such a case, to contact the subject 100, for example, by telephone to clarify why the subject 100 has not performed the test as instructed and to impress upon the subject the importance of performing the test as indicated.

"Moving pattern" Test Method

The method disclosed hereinbelow is based on the presentation of a first pattern at a first location on the surface of a display device (such as, but not limited to the screen 112 of the display device 115) to the patient or the test subject.

After the patient fixated on a fixation target presented on or adjacent to the first pattern, the first pattern disappears from the first location of the display device and a second pattern is presented at a second location on the display device. The second pattern may be identical to the first pattern (except for the fact that it appears at a different location on the display device) or it may be different from the first pattern by having one or more portions thereof changed or altered. Such changes or alterations may include distortion of the shape or elimination of one or more portions of the first pattern, or changes in the color or appearance of one or more portions of the first pattern. Because the first pattern is made to disappear from the first location on the display device and the second pattern appears at a second location of the display device different than the first location, the patient or test subject may visually perceive this as a movement or jump of the pattern from the first location to the second location on the display device, in other words, the patient may perceive a pattern "jumping" on the screen of the display device from a first to a second location even though the pattern does not actually move on the display device (the pattern actually disappears from a first location on the display device and appears at a second location on the display device). This is why this particular embodiment of the testing method is referred to as the "moving pattern" or "jumping pattern" test hereinafter.

Figure 2A:
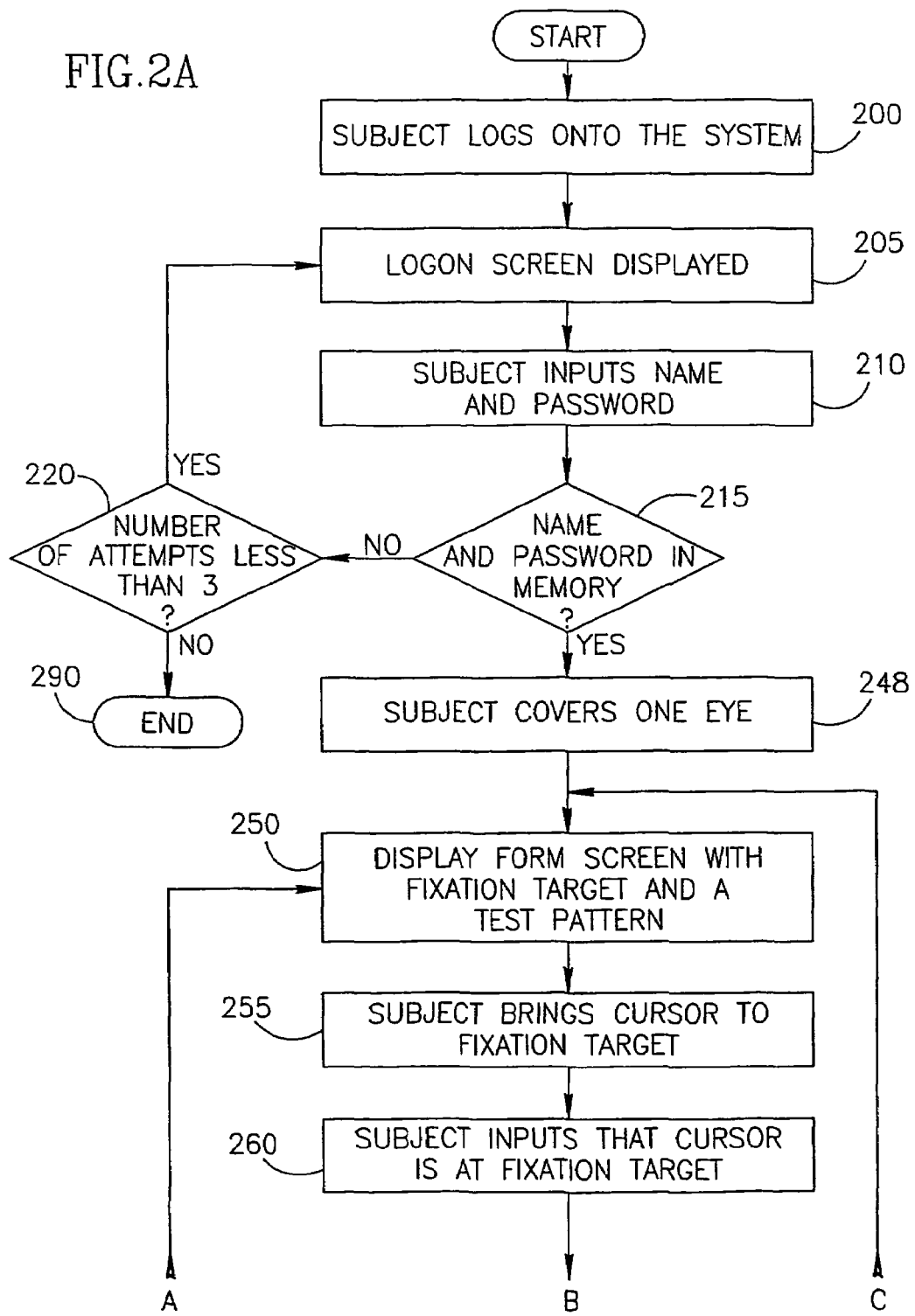
FIG. 2 is a schematic flow chart diagram illustrating a method of executing an eye test for detecting an eye disease using a system such as the system illustrated in FIG. 1, in accordance with an embodiment of the present invention.
Figure 2B:
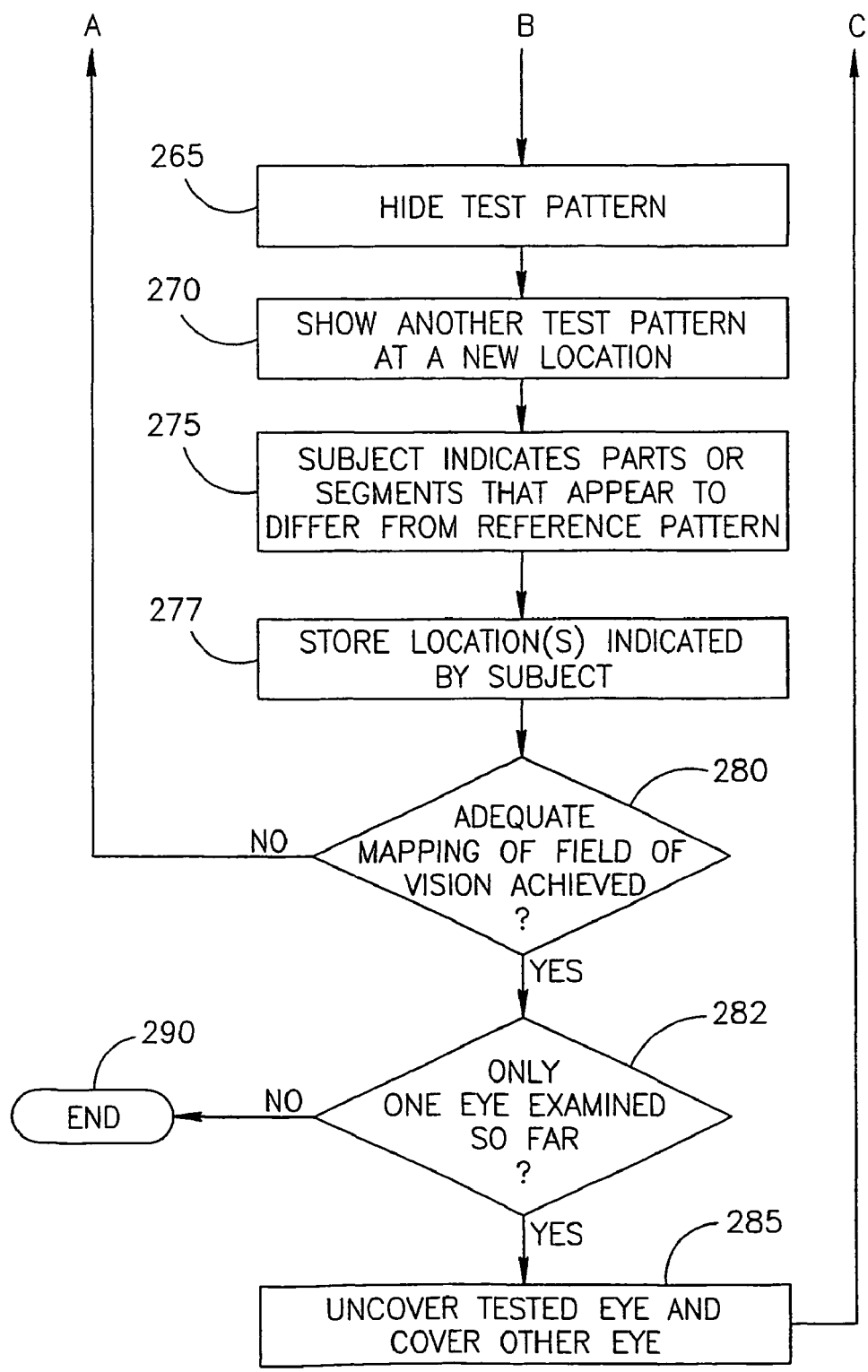

FIG. 2 is a schematic flow chart diagram illustrating a method of executing an eye test for detecting an eye disease using a system such as the system illustrated in FIG. 1, in accordance with an embodiment of the present invention.

Figure 3:
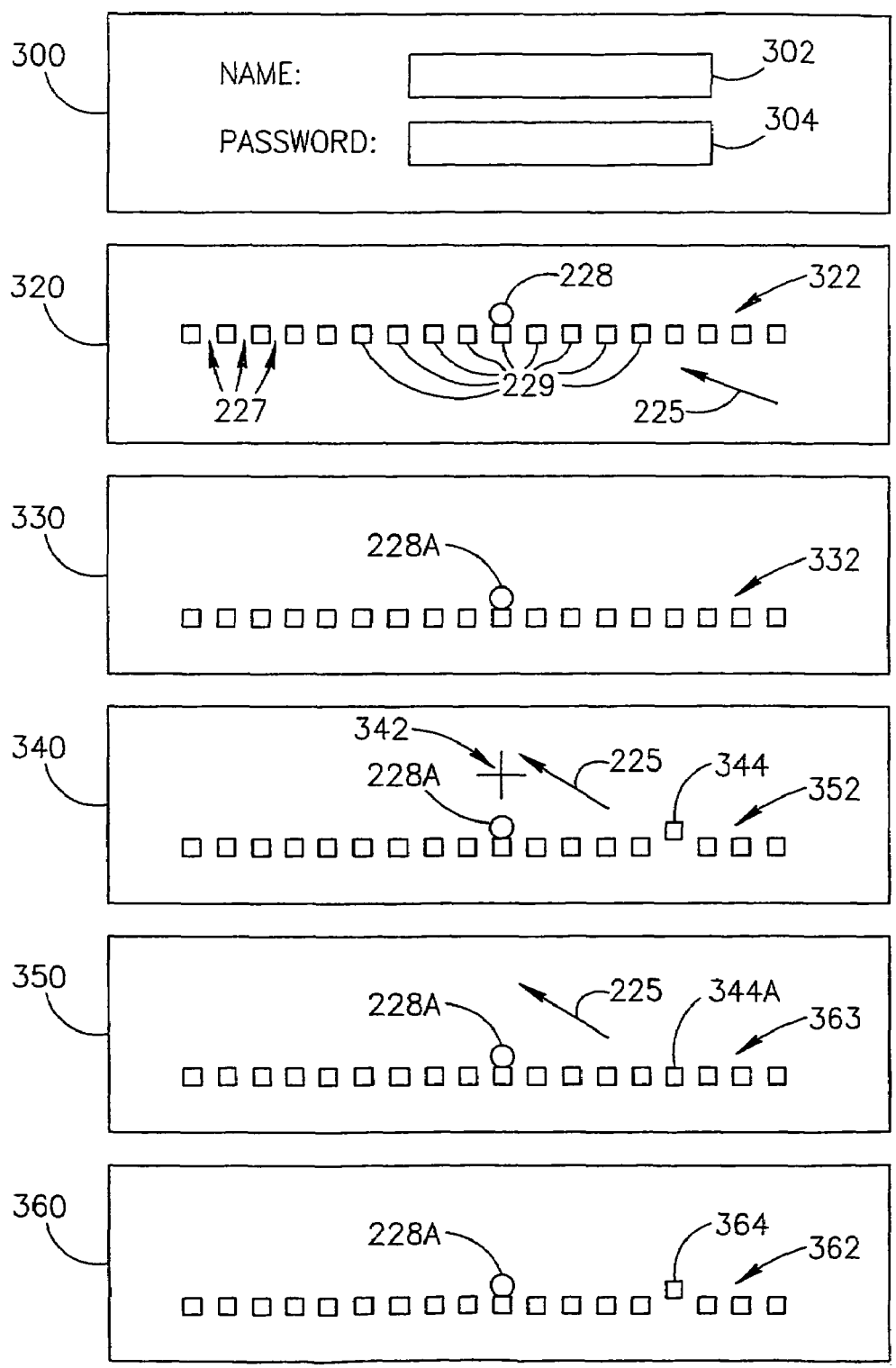
FIG. 3 schematically illustrates selected exemplary screen representations including exemplary test patterns which may be presented to a tested subject, in an exemplary embodiment of the testing method of the present invention, and selected schematic representations of how the test patterns may be perceived by a tested subject in selected stages of the testing.

FIG. 3 schematically illustrates selected exemplary screen representations including exemplary test patterns which may be presented to a tested subject, in an exemplary embodiment of the testing method of the present invention, and selected schematic representations of how the test patterns may be perceived by a tested subject in selected stages of the testing.

FIG. 3 includes schematic screen diagrams 300, 320, 330 and 360 (also referred to as screens 300, 320, 330 and 360 hereinafter) which schematically illustrate the patterns displayed on the screen 112 of the subject's display device 115 at various different exemplary steps of the eye test performed by the system illustrated in FIG. 2, and schematic screen diagrams 340 and 350 (also referred to as screens 340, and 350 hereinafter) which schematically illustrate the possible appearance of the screen 112 as may be perceived by the tested subject at some exemplary steps of the eye test. It is noted that screen 300 of FIG. 3 which does not include test patterns, schematically represents a possible log-on screen which may be presented to the test subject.

It is noted that the exemplary schematic screens 300, 320, 330, 340, 350, and 360 of FIG. 3 are schematically drawn for illustrative purposes only and are not drawn to scale. Additionally, the sizes of the various patterns, pattern segments, fixation targets, are not drawn to scale, and their sizes and their relation to the screen size are arbitrarily shown for illustrative purposes only.

Turning to FIG. 2, in step 200, the subject 100 may log onto the computer system 105. The processor 135 may cause log-on screen 300 to be displayed on the subject's display device 115 (step 205). The log-on screen 300 prompts the subject to input his name into a field 302 and to input a previously assigned password into a field 304 for accessing the processor 135. In step 210 the subject inputs his name and password using computer input devices such as the keyboard 120 or the mouse 125. The processor 135 then checks whether the inputted name and password are stored in the memory 145 (step 215). If the inputted name and password do not match a corresponding name and password which are stored in the memory 145, the processor 135 determines whether the number of attempts the subject has made to input a name and password is less than a predetermined number of attempts such as, for example, three attempts (step 220). If yes, the process returns to step 205. If no, the process terminates.

If at step 215 the processor determines that the name and password are in the memory 145, the process continues in step 248 by the subject being instructed to cover an eye, so that the test is performed using one eye only. The subject may be instructed to cover an eye by displaying appropriate text (not shown) or a drawing (not shown) or an icon (not shown), or a graphic element (not shown) or any combination thereof on the screen of the display device 115.

It is noted that the tested subject 100 may be asked to cover a specific eye (for example, the subject may be asked to cover the right eye and to view the screen 112 with the uncovered left eye for testing the left eye). In this way the computer system 110 may automatically record that the left eye is being tested. Alternatively, the tested subject 100 may be asked to mark or input or otherwise indicate which eye is to be tested, such as, for example, by clicking a cursor on one of two boxes (not shown) which may be presented on the log-on screen 300 or on any other suitable screen presented to the subject before the test begins. In such a case the test results may be labeled as taken from the eye selected by the subject 100.

In step 250 a form screen 320 is displayed in which a pattern such as the segmented line 322 is displayed. This is by way of example only, and other suitable patterns may be used within the scope of the invention. The pattern may comprise a single component, or may comprise several components which may or may not be all identical. Thus, the pattern may comprise several lines, one or more circles, lines and circles together, or any other suitable combination of pattern elements, including but not limited to one or more straight lines, dotted lines, curved lines, linear or non linear segments, dots, and other various geometrical patterns such as but not limited to circles, arcs, rectangles, squares, triangles, and the like. The screen 112 of the display device 115 may display a visually noisy background to the displayed pattern. The line 322 may be composed of several short segments 229 separated by gaps 227. Alternatively, the displayed line may be continuous (not shown).

Preferably, the length of the line 322 is such that when the tested subject's eye is at a distance of approximately 50 centimeter from the screen 112 of the display device 115 the length of the line 322 corresponds to a cone angle of 1-20°. It is noted that while in most tests the length of the lines used corresponded to a cone angle of 14°, other different line lengths may be used. At these viewing conditions, each of the gaps 227 between the segments 229 (the distances separating two adjacent segments 229) may correspond to a cone angle of between 1 minutes arc to about 2° (two degrees). Other, different line lengths and gap sizes may however also be used. For example, if the test pattern is a continuous line there are no gaps.

It is also noted that if test patterns which comprise a continuous line are used, no segments are used and there are therefore no gaps.

If the pattern consists of two or more parallel lines, the spacing between the lines corresponds, preferably, to a cone angle from about 10 to about 600 minutes arc. The test patterns may be horizontal patterns such as, but not limited to the horizontal line 322 illustrated in screen 300, but may also be vertical patterns such as but not limited to a vertical segmented line (not shown) or slanted patterns such as but not limited to a slanted segmented line (not shown). A fixation target 228 may be displayed on the screen adjacent to one of the segments 229. The fixation target may be a circular pattern such as the circular fixation target 228 of screen 320 of FIG. 3, or may have any other shape or pattern suitable for serving as a fixation target for focus the tested eye thereon, such as but not limited to a square pattern, a triangular pattern, or any other suitable pattern which is suitable for functioning as a fixation target.

It is noted that while the fixation target 228 illustrated in FIG. 3 is a circular pattern which appears close to the middle segment of the line 322, other different forms of the fixation target may be used. For example, the fixation target may be implemented as a hollow (unfilled) circle (not shown) surrounding the middle segment of the line 322 or superimposed thereon, or as any other suitable pattern which is positioned close to or is superimposed upon the line 322.

Generally, the shape of the fixation target may depend, inter alia, on the shape and dimensions of the test pattern which is being used in the test. The fixation target may have the same color of the test pattern (such as, for example, the segmented line 322) or may have a different color than the color of the test pattern. In accordance with another variation, the fixation target may be the central (middle) segment of the line 322, in which case the middle segment may or may not have a color which is different than the color of the remaining segments 229 of the line 322 in order to make easily identifiable by the test subject.

In the example in which a single segmented line serves as the test pattern, the subject may be instructed to bring a cursor 225 appearing on the screen to the fixation target 228. In order to aid the subject, the movement of the cursor 225 may be restricted to a line (not shown) which is parallel to the line 322 so that the cursor 225 always points to one of the segments 229.

The subject 100 may be asked (for example, by an instructor, a physician an ophtalmologist or any other person training the subject in performing the test) or otherwise instructed (such as for example by displaying appropriate messages or text an the screen 112 of the display device 115) to point the cursor 225 at the fixation target 228. The subject 100 may perform this pointing in step 255 by using a computer device such as the keyboard 120, or more preferably the mouse 125. Other pointing devices may also be used for pointing, such as but not limited to, a digitizing tablet in conjunction with a stylus, a finger, a light pen in conjunction with a touch screen, or any other suitable pointing device or suitable input device known in the art.

The fixation target 228 may be sized so that it is large enough to be seen by the patient or test subject but small enough so that bringing the cursor 225 to the fixation target 228 is a demanding task for the test subject. This causes the subject to fixate his vision on the fixation target 228. Upon bringing the cursor to the segment 229, the subject may provide a suitable indication that he has positioned the cursor 225 to point at the fixation target 228. For example, the patient or test subject 100 may provide the indication by clicking on the mouse 125 or by depressing a predetermined key on the keyboard 120 (step 260). This input may serve as an indication or a verification that visual fixation has been achieved. It is noted that the size of the fixation target 228 may depend, inter alia, on the distance of the tested eye from the screen 112.

It is noted that if the subject is using a pointing device and/or an input device which is different than the mouse 125 or the keyboard 120, the subject may indicate fixation on the fixation target 228 by performing any other suitable action. For example, if a touch screen (not shown) is used as an input device, the subject may touch the touch screen (not shown) with a light pen (not shown), or with a stylus (not shown) or with a finger (not shown) at the position at which the fixation target is displayed. Other suitable forms of indicating or confirming fixation may be used, depending, inter alia, on the input device or pointing device which is being used When the subject signals (for example, by clicking a button on the mouse 125, or by any other suitable way) that the cursor 225 is positioned to point at the fixation target 228, indicating that his vision is fixated on the fixation target 228, the line 322 is made to disappear from the screen 320 (step 265). After a predetermined delay time interval (for example a delay interval in the range of 0 to 200 milliseconds), a second pattern such as the segmented line 332 is made to appear (displayed) on the screen 112 at a location different than the location of the line 322 as shown in screen 330 (step 270) so as to allow the subject to form a perceived image of the segmented line 332. In this example, the segmented line 332 is similar to the line 322 but appears on the screen 112 at a location which is different than the location of the line 322.

It is noted that if the duration of the delay time interval is zero, the line 332 is presented on the screen 112 immediately after (or within the short time required by the computer 100 to process the subject's input and display the line 332 on the screen 112) the subject 100 indicated fixation. In most of the experimental eye tests conducted in patients no delay was used (the delay time interval was zero).

The line 332 may, for example, be parallel to the line 322. Since the subject's vision had been fixated on the fixation target 228, the line 332 will appear in the periphery of the subjects field of vision. Any disturbance in his vision due to a retinal lesion (such as but not limited to a lesion caused by AMD or diabetes or by other different pathological eye conditions) may be apparent to the test subject as a difference between the perceived image of the second pattern and a pre-defined reference pattern, which in this example is provided by the first pattern (the segmented straight line 322).

Additionally, or alternatively, the tested patient or subject 100 may have been told by a trainer (such as, for example, by an ophtalmologist or other medical or paramedical personnel) before the beginning of the test that he or she is going to be presented with test patterns which will look like a segmented straight line. In such a case, the subject 100 may conceive a "virtual" predetermined reference pattern which in this particular example of the test is a conceived image of a straight segmented line. The word "virtual" is used herein to indicate that the predetermined reference pattern is mentally conceived by the patient or test subject without having to actually present the patient with the test pattern. In other words the understanding of the patient of how the reference pattern (such as, for example, the straight segmented line of the example illustrated in FIG. 3) is supposed to look like may be based on the previous visual experience of the patient or test subject.

The explanation to the patient of what the reference pattern is going to look like may be advantageous, since in a small percentage of patients it may happen that in the first presentation of the first test pattern (such as for example in the initial presentation of the line 322) the image of the test pattern may fall on a lesioned retinal region. In such a case, the perceived image of the test pattern may be distorted.

Therefore, in such a case, the perceived image of the initially presented line 322 is not usable as a reference pattern and the patient may see or detect a difference between the perceived image of the line 322 and the (virtual) reference image which the patient has been told to expect.

The difference between the perceived image of any of the test patterns (including, but not limited to, the lines 322 and 332) which may be presented to the patient and the reference pattern may be perceived by the test subject 100 in various different ways. Thus, as the line 322 is perceived by the subject to jump or move to the new location on the screen 112 one or more of the segments 229 of the line may seem to the subject not to arrive at their new position on the line 332 (of the screen 330) at exactly the same pace or contour as the other segments. In other words, one or more portions or segments of the line may temporarily seem to lag or to move differently relative to the other parts or segments of the perceived line. This may also be perceived by the subject as if one or more portions of the perceived line were wavy or moved or bulged for a short while or as if one or more of the segments or line portions deviated from the reference pattern (which is a straight segmented line, in the exemplary and non-limiting example of FIG. 3) before assuming again the perceived appearance of the reference pattern. Additionally or alternatively, depending, inter alia, on the nature of the retinal lesion present, one or more portions or segments of the perceived image of the test pattern (such as, for example, one or more the segments 229 of the perceived line 322) may appear to temporarily change their apparent brightness (such as becoming brighter or becoming darker), or change their color temporarily as the line moves or jumps, and then return to their originally perceived brightness or originally perceived color, respectively. Additionally or alternatively, one or more of the segments 229 or portions of the test pattern may appear to momentarily or temporarily become blurred or smeared.

Additionally, various different combinations of this differences may also be perceived by the subject. For example one or more of the segments or portions of the test pattern may appear to lag or move differently than the other segments or portions of the pattern and also to change their perceived brightness. Other different combinations of differences may also be perceived by some patients.

For example, when the subject's vision is fixated at the location where the fixation target 228 had previously appeared (represented by the crossed lines 342 in screen 340), a segment 344 of the line 332 may appear to be out of line with other segments in the line 332 or may be otherwise distorted, blurred, shifted or discolored. It is noted that the screen labeled 340 of FIG. 3 represents the screen 112 and the pattern 332 as perceived by the tested subject. In other words, the illustrated line 332 with the shifted segment 344 are shown as perceived by a subject or patient having a retinal lesion and not as actually displayed on the screen 112. Thus, while the screen 330 of FIG. 3 schematically represents the image as actually presented to the subject 105 on the screen 112, the screen 340 of FIG. 3 represents the image perceived by a subject having a retinal lesion (in the tested eye) after the line 332 of screen 320 is made to disappear (hidden) and the line 332 of screen 330 is presented (or displayed) to the subject at a different location on the screen 112.

Screen 340 (of FIG. 3) illustrates a possible appearance of the line 332 (of screen 330) to an individual having a retinal lesion. The perceived line 352 of the perceived screen 340 represents the image of the line 332 presented in screen 330 as it may be perceived by an individual having a retinal lesion. The segment 342 of the perceived line 352 may typically be temporarily perceived as being out of line with other segments in the line 352. This is by way of example only, and other differences between the perceived image and the pre-defined reference pattern may be perceived, such as, but not limited to, one or more segments in the second pattern appearing to the subject as being shifted or wavy or lagging behind, or blurred, or dimming, or smeared, or bent, or otherwise distorted, or discolored. Additionally, one or more of the segments in the second pattern may be perceived by the subject to disappear or to be missing from the second pattern. As the subject subsequently shifts his vision from the fixation target 228 to the presented line 332, the segment 344 in the image of the perceived line 352 may appear to move into alignment with other segments in the line 332 as shown in screen 350. Thus, the line 363 of screen 350 (FIG. 3) schematically represents the perceived image of the line 322 as possibly perceived by the subject having a retinal lesion after the subject re-fixates his vision on the line 332. Thus, the segment 344A schematically represents the new perceived position of the previously perceived segment 344 after the patient shifted his eye to refixate on the new position of the line 332. The perceived segment 344A may now be perceived as realigned again with the rest of the perceived segments of the perceived line 363.

Typically, the reason for the presented line 332 being perceived as straight again (as illustrated in the perceived line 363 of screen 350) after the patient refixated his vision at the new position at which the line 332 appeared after the line 322 disappeared from the screen, is that in most cases when the subject shifts his vision from the fixation point 228 to the new location on the screen at which the line 332 appeared, after a certain time (typically a few hundred milliseconds or longer) the "filling-in" phenomenon disclosed hereinabove may occur.

The subject, in step 275, may indicate which, if any, of the segments in the line 332 appeared different or were perceived to behave differently than corresponding segments in the predefined reference pattern. This may be done by the subject bringing the cursor 225 to the segment or segments that appeared to move or to blur or to distort or to disappear, or to otherwise change (the segment 344 in this example) and clicking a button on the mouse 125 or a key on the keyboard 120, or by otherwise performing an action with a pointing device (not shown) or any other suitable input device. The data representing the location(s) on the screen 112 of the segment or segments in the region pointed to by the subject may thus be stored by the system (step 277) in the memory of the computer system 105, and/or in the memory 145 of the server 140 or by any other suitable storage means, such as but not limited to, a fixed or removable magnetic media storage device (Hard disc drive or floppy disc drive), optical storage device, magneto-optical storage device, holographic storage device or any other suitable storage device known in the art. This stored data may be used to locate and/or report and/or display and/or symbolically represent (in hard copy or otherwise), the region in the subject's retina in which the retinal lesion is located, as disclosed in detail hereinafter. It is noted that the storage device or memory used for storing the test results data may be included in or suitably linked or coupled to the computer system 105 or the computer 110, or the server 140. Alternatively, the storage device may be a shared device which is shared by or accessible to one or more of the computer system 105 or the computer 110, or the server 140, over a communication network. Thus, while the test results data may be stored locally on the system 105, this is not obligatory and the test results may be stored elsewhere as disclosed hereinabove.

In step 280 it is determined whether adequate mapping of the field of vision was achieved. For example, it may be checked whether the number of lines 322 presented to the subject is less than a predetermined number, such as, for example, 40 (or any other suitable predetermined number). If the number of lines 322 presented to the subject is less than the predetermined number, the process may return to step 250 and a new line 322 is presented to the subject. Steps 250 to 280 may be repeated several times, for example 40 times (or any other suitable predetermined number of times suitable for such a test). In each repetition the line 332 may be presented at a different location of the screen 112 until the region of the subject's macular visual field has been appropriately mapped.

It is noted that such mapping may be achieved in more than one way. For example, in accordance with one preferred embodiment of the invention, after the line 332 is presented or displayed to the subject 100, and the subject has finished marking the segments which appeared different than the corresponding segments of the line 322, or alternatively to mark the segments which appeared different than the "virtual" predetermined reference pattern (a straight segmented line mentally conceived by the subject), the subject may visually fixate the tested eye on a fixation target 228A (see screens 330, 340, 350 and 360) in the vicinity of the line 332, by bringing the cursor 225 to point at the fixation target 228A and clicking a button on the mouse 125 to indicate fixation as disclosed in detail hereinabove. This may trigger the repeating of steps 265 and 270 which will result in the disappearing of the line 322 and the showing of a new line (not shown) at a new position on the screen 112 which is different than the position at which the line 332 was previously presented. The subject may then proceed to mark any segments at which a difference was perceived as disclosed hereinabove. The presentation may be similarly continued until adequate mapping of the field of vision has been performed.

Alternatively, in accordance with another embodiment of the present invention, after the line 332 is presented or displayed to the subject 100, and the subject has finished marking the segments which appeared different than the corresponding segments of the line 322, or alternatively to mark the segments which appeared different than the "virtual" predetermined reference pattern (a straight segmented line mentally conceived by the subject), the line 332 may be caused to disappear from the screen 112, and the line 322 and the fixation target 228 may be again presented to the subject 110 in the same positions illustrated in screen 320. The subject may then again fixate on the fixation target 228 by bringing the cursor 225 to point at the fixation target 228 and click the mouse 125 to indicate fixation. The computer 100 may then present a new test pattern (not shown) at another new position relative to the position of the line 322 and the process may repeat after the subject marked any segments for which a difference was observed. By randomly or pseudo-randomly selecting a new line position for each new repetition the process may thus achieve adequate mapping of the desired macular area.

It is noted that if the first test pattern (such as for example the straight segmented line 322) which is presented to the subject happens to be projected on a region of the retina which is lesioned, the subject 100 may initially perceive the pattern to be distorted or modified but after a certain time the test pattern may be perceived to be identical with the predetermined reference pattern (such as for example a straight non-distorted segmented line due to the "filling in" phenomenon disclosed hereinabove. In such a case, the subject 100 may indicate or mark the location of the initially perceived distorted or modified region or component of the first test pattern, by using the mouse 125 and the cursor 225 as disclosed hereinabove. Alternatively, the subject 100 may be instructed (before or during the test) to ignore the initially perceived distortion or modification and to proceed to perform the fixation on the fixation target 228 as disclosed hereinabove by bringing the cursor 225 to point at the fixation target 228 and clicking a button on the mouse 125. When the second test pattern, such as the line 332 is then presented at another location on the screen 112 (see screen 330 of FIG. 3), the subject 100 may temporarily perceive a modification or distortion as the subject 100 shifts his vision from the fixation target towards the location of newly presented test pattern (which in this example is the location of the line 332 of screen 330 of FIG. 3). Therefore, in such cases in which the image of the first test pattern falls on a lesioned retinal area, the subject may perceive a distortion or modification in each of the repetitions or iterations of the test, irrespective of the location at which the second test pattern is presented on the screen 112. The distortion will be perceived after the patient shifted his vision from the fixation target towards the test pattern presented at the new location due to the fact that the shifting causes the image of the newly presented test pattern to be projected on the lesioned retinal area. Because of this phenomenon, the subject may mark a distortion or modification on all the second test pattern repetitions, and all of the marked distortions will tend to be marked at positions along the test pattern which approximately correspond to the position of the distortion or modification which was initially perceived at the first time of presentation of the first test pattern due to the presence of the retinal lesion.

It is noted that if the test results do exhibit such an approximate "alignment" of multiple markings of perceived distortions or modifications at approximately similar positions on the test pattern, irrespective of the location of the presented second test patterns, this may be taken as an indication that there is at least one suspected retinal lesion at a position in the retina on which the image of first test pattern was projected.

It is further noted that while the presence of a retinal lesion may be detected in the above case, it may be advisable to test the same eye of subjects exhibiting such a spurious marking "alignment" using the "flash test" embodiment of the invention as disclosed in detail hereinafter, since this test does not show this spurious marking "alignment" phenomenon.

It is noted that while it is possible to perform the testing by mapping the field of view of the patient using only horizontal line patterns (such as the line 322) and moving the horizontal line patterns vertically to different positions on the screen 112, the mapping may also be performed using vertical lines (not shown in FIG. 3) which may be moved horizontally to different positions on the screen 112. It may also be possible to use a plurality of orthogonal horizontal and vertical lines in the same mapping test, in which case the mapping coverage of the field of vision may resemble a grid of intersecting lines (not shown).

Furthermore, the mapping of the field of view may also be done using a series of lines that are inclined at an angle to the horizontal or vertical orientation (slanted lines), or combination of series of slanted lines which may intersect each other either orthogonally or non-orthogonally, such that if these lines were all displayed at the same time on the screen 112 they may form a grid of intersecting lines (not shown).

It is noted that in step 280 it is checked whether adequate mapping of the field of vision of the tested eye has been achieved. For example, if the location of presentation of the test pattern is different at each repetition or iteration of the test, adequate mapping may be ensured by checking that the number of lines presented to the subject has reached a predetermined number of iterations ensuring that data has been collected which suitably covers or maps the entire field of vision at a desired resolution.

Other different methods may however also be used to check adequate mapping. For example, if the testing of each location needs to be repeated more than one time and the location of presentation of test patterns is randomly or pseudo-randomly selected, the locations of performed tests may be compared with a look-up table to verify that the desired number of test repetitions for each test pattern location has been performed. If adequate mapping has not been achieved the process may return control to step 250 to present the next test pattern.

If adequate mapping of the field of vision of an eye has been achieved, the process may proceed by determining whether only one eye has been examined so far (step 282). If only one eye has been examined, the subject may be instructed to uncover the non-examined eye and to cover the examined eye (285). The process may then return to step 250 with the subject testing his other eye as disclosed in detail hereinabove. If both eyes have been examined, the process may terminate (step 290).

The position of the line 322 presented or displayed to the subject on the screen 112 may thus be varied in order to appropriately cover the macular area at a desired resolution so as to detect lesioned retinal regions. It is noted that in accordance with one preferred embodiment of the invention, the mapping may be performed more than once, and that the central part or fovial region of the macular area of the retina may also be mapped at a higher resolution than the rest of the macular area. This may be accomplished by presenting to the subject test patterns such as the line 322 at locations which are relatively close to one another on the screen 112. This may result in higher lesion mapping resolution in the fovial region.

Figure 4A:
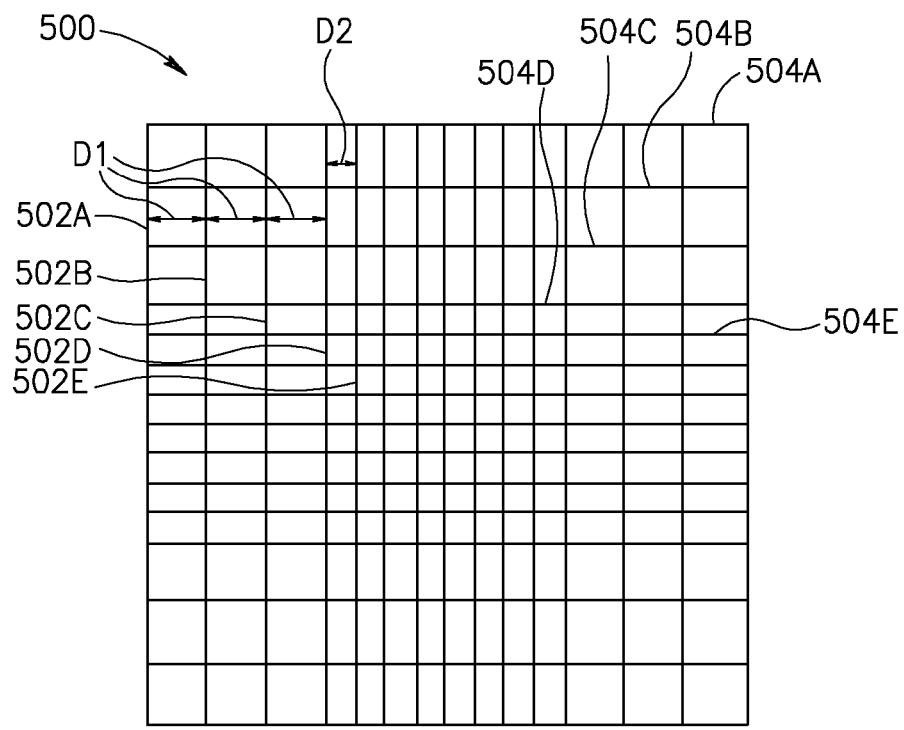
FIGS. 4A-4B are schematic diagrams illustrating some exemplary types of line series which may be useful for mapping retinal lesions in accordance with some exemplary embodiments of the present invention.
Figure 4B:
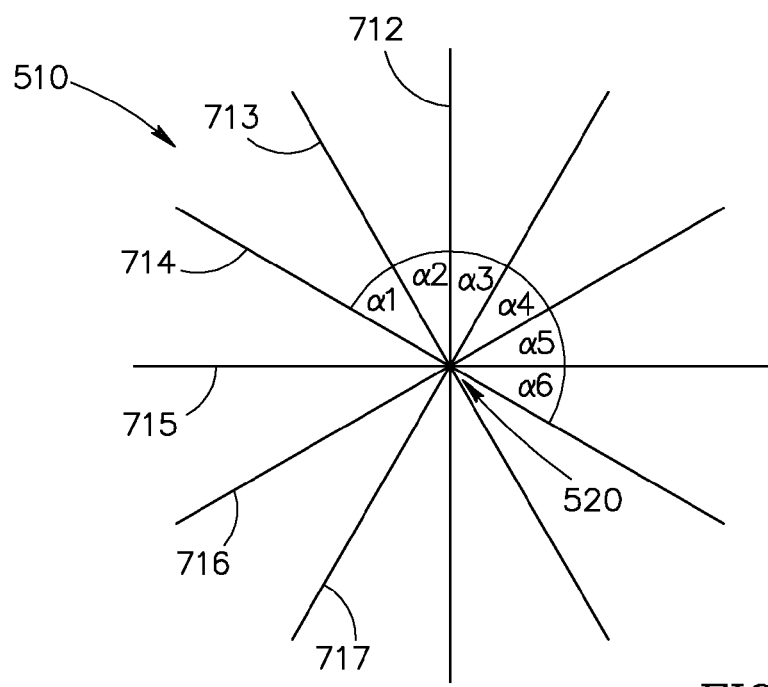

Reference is now made to FIGS. 4A-4B which are schematic diagrams illustrating some exemplary types of line series which may be useful for mapping retinal lesions in accordance with some exemplary embodiments of the present invention.

FIG. 4A schematically represents a mapping grid which may be formed if all the linear test patterns used in the were to be simultaneously presented on the screen 112. The grid 500 thus formed may include parallel vertical lines, such as for example the vertical lines 502A, 502B, 502C, 502D, and 502E and parallel horizontal lines, such as for example the vertical lines 504A, 504B, 504C, 504D, and 504E. It is noted that the horizontal lines need not be equally spaced from each other. For example while the line pairs 502A and 502B, 502B and 502C, and 502C and 502D may be separated from each other by a cone angle D1, the line pairs 502D and 502E may separated from each other by a cone angle D2. Preferably D1 is larger than D2, such that the dens of grid lines at the central region of the grid 500 is higher than the density of e lines at more peripheral regions of the grid 500. This may enable mapping of the central fovial region at a higher mapping resolution than the mapping of more peripheral fovial regions. It is noted however, that the horizontal and vertical lines of the grid 500 may be also equally spaced from each other or may be arranged differently than the arrangement of the lines illustrated in FIG. 4A. Furthermore, it is noted that while the lines of the grid 500 may be contiguous lines as shown in FIG. 4A (for the sake of clarity of illustration), the lines of the grid 500 may also be segmented lines (not shown) or dotted lines (not shown) or the like. Orthogonal or non-orthogonal slanted lines may also be used (not shown) to map the retina.

The grid used for mapping may also include only the horizontal lines shown in grid 500 or only the vertical lines of grid 500. Furthermore, It is noted that the number and the density of the lines shown in FIG. 4A is only shown by way of example and the number of the lines as well as the separation between the lines may be modified may be changed depending, inter alia on the required retinal mapping resolution.

FIG. 4B schematically represents a mapping grid 510 which may be formed if all the linear test patterns used in the were to be simultaneously presented on the screen 112. The grid 510 thus formed may include a plurality of lines 712-717 which intersect at a point. While the lines 712-717 are illustrated as having identical lengths, their lengths may also vary. The angles $\alpha 1$, $\alpha 2$, $\alpha 3$, $\alpha 4$, $\alpha 5$, and $\alpha 6$ may be identical to each other and may be all equal to 60°. It is noted, however that the number of lines in the grid and the angle at which each line is inclined relative to the horizontal line 715 may vary and may be different than the values illustrated in FIG. 4B. Additionally, the number of the lines may vary such that the grid may include more or less than the six lines 712-717. While the lines 712-717 are illustrated as contiguous (for the sake of clarity of illustration), the lines may also be segmented or dotted lines, or the like.

It is furthermore noted that many variations and permutations of the test patterns of the invention are possible which are all considered to be within the scope and spirit of the present invention. Similarly, the number of the test patterns forming the mapping grid may vary as may their separation from each other, their angular inclination within the mapping grid.

It will be apparent to those skilled in the art that the exemplary mapping grids 500 and 510 do not represent the form or shape of a single test pattern but are rather virtual representations of the images that would result if all the test patterns of exemplary possible tests were to be projected simultaneously on a surface.

In accordance with another embodiment of the invention, it is also possible to present to the subject test patterns which include a distortion or other modification of the predefined reference pattern. For example, while the line 332 of screen 330 of FIG. 3 comprises segments which are all arranged or aligned in a straight line, a line 362 actually having a displaced segment 364 may also be presented to the subject on the screen 112 as illustrated in screen 360 of FIG. 3. The line 362 may be presented, for example, for a duration of up to about 300 milliseconds, but other suitable presentation duration time values may also be used.

Generally, test patterns, such as for example the line 362 of screen 360 (FIG. 3) may be regarded as test patterns which include an intentionally introduced distortion which may be similar to distortions which may be seen or perceived by a patient having a retinal lesion when a non-distorted test pattern (such as, but not limited to the line 332 of screen 330) is presented to the patient. Such test patterns including a distortion may also be referred to hereinafter as "artificially distorted" test patterns. The presentation of such artificially distorted test patterns may be used, inter alia, to ascertain that the subject is aware of the visual distortion associated with a retinal lesion, and that his responses reliably reflect the perceived appearance of lines presented to him.

It is noted that while in the exemplary artificially distorted line 362 illustrated in screen 360 of FIG. 3 only one segment 364 is shifted relative to the other segments of the line 362, other different types of distortions may be used. In accordance with other exemplary embodiments of the inventions such distortions may comprise but are not limited to displacing or mis-aligning more than one segment relative to the rest of the segments (not shown), tilting or changing the orientation of one or more segments relative to the orientation of the remaining segments (not shown), bending or otherwise changing the shape of one or more segments segment, removing one or more of the segments (not shown), blurring one or more of the segments (not shown), changing the hue or color or brightness of one or more segments of the test pattern (not shown), or introducing other types of alterations to the test pattern which may resemble distortions or alterations which may be perceived by a person having a retinal lesion when such a person is presented with a non-distorted test pattern or reference pattern.

It is noted that if the test patterns used in the test are non-segmented, such as for example if the test pattern comprises a contiguous (non-segmented) straight line (not shown), the artificially distorted test patterns may include but are not limited to bending one or more portions of the contiguous line such that these portions are not straight (for example, such distorted portions of the test pattern may be curved or wavy), blurring or smearing one or more portions of the test pattern (not shown), hiding (not presenting) one or more portions or parts of the test pattern (not shown) or changing the hue or color or brightness of one or more portions of the test pattern, or the like. Other suitable visually perceivable types of distortions or alterations of test patterns may also be used.

The presentation of such artificially distorted or otherwise intentionally altered or modified test patterns to the patient or test subject may also be advantageously used to detect cases in which the patient is not paying attention to the test patterns due to fatigue or due to any other reason. This may enable the assessment of the degree of reliability of the test result. For example, if the patient does not reliably and/or accurately report the presence of the distortion or alteration in such artificially distorted or otherwise altered test patterns presented to him during the testing, this may be taken as an indication of a problem and may indicate a possible need to repeat the test or alternatively to label the test results as unreliable. Additionally, the degree of correlation between the location of the distortion or alteration on the presented test pattern and the location of the distortion or alteration perceived and marked (or reported) by the patient may be a used to assess the accuracy of perceiving and/or of the reporting of the location of the distortion or alteration by the patient or tested subject.

It is noted that in the exemplary screen 320 of FIG. 3, the segmented line 322 may be regarded as a predetermined "reference pattern" of the test. The patient may be asked and/or trained to relate to the perceived image of the presented straight segmented line 322 as the reference pattern against which to compare the perceived images of the later presented test patterns. When the test is first presented to a patient, the patient may be told by the trainer or the individual administering the test that he is about to be shown a straight segmented line (or any other reference test pattern which is being used for the test). In this way, the patient becomes aware of the reference pattern against which he is expected to compare the perceived images of the test patterns which are going to be presented to him as the testing proceeds. It is noted that the patient may also be told before the testing begins that he is to be presented with straight segmented lines (without initially presenting to him such a line) and asked to compare the perceived image of each of the lines presented to him with a reference pattern which is a straight segmented line.

It is noted that the testing method of the present invention is not limited to the "moving pattern" testing method disclosed hereinabove, and may be modified in different ways, which are considered to be within the scope of the present invention.

"Flash test" Method

In this embodiment of the invention, a fixation target is presented to the tested individual on a display device, such as but not limited to the screen 112 of the display device 115 (FIG. 1). After the tested patient has fixated on the fixation target, a test pattern is briefly presented (flashed) at a first location on the display device for a time duration which is sufficient to allow the patient to perceive an image of the presented test pattern. The image perceived by the patient in also referred to as a "perceived image" of the test pattern. The patient may then be requested to indicate whether he or she detected a difference between the perceived image of the presented test pattern and a reference pattern.

The tested patient may be informed by the trainer, or ophtalmologist or the person delivering the test, before the test is performed that he is going to be presented with patterns similar to or different than a reference pattern. The patient may or may not be actually presented with the reference pattern before the test begins. For example, if the reference pattern is a straight segmented line, the patient may be verbally told that he is going to be presented with a variety of test patterns that may be similar to or may be different from a straight segmented line, without showing the patient a straight segmented line (which is the reference pattern in this non-limiting exemplary test) prior to the presentation of the actual test patterns to the patient. In such a case, the reference pattern is based on the prior acquaintance of the patient with the reference pattern which is used. In other words, previous knowledge of the patient of how a straight segmented line looks is relied upon.

It is also possible (though not obligatory), however, to present the reference pattern the patient before the actual test patterns are presented in order to give the patient an idea of how the reference pattern is supposed to look like. While this may help the patient to understand and familiarize himself or herself with the form of the reference pattern, it is not a necessary part of the test, since most patients may adequately perform the test just by being told verbally what the reference pattern is without being presented with the actual reference pattern prior to the presentation of the test patterns.

After the patient is presented with a test pattern, if a difference was detected by the patient between the pattern perceived by the patient as a result of the presentation of the test pattern and the reference pattern, the patient may indicate the region or regions or segments or components of the perceived pattern at which a difference or differences were noticed. The presence and the location of the difference(s) which are detected and indicated by the patient may be stored for further processing and analysis as disclosed hereinabove. This procedure may be repeated several times while changing the location of the test pattern relative to the fixation target on the screen 112. The number of repetitions and the location of the presented test patterns are such that a suitable area of the visual field of the tested eye of the patient is mapped for detection of possible retinal lesions or pathologies.

Reference is now made to FIGS. 5A-5J which are schematic diagrams illustrating the patterns displayed on the screen 112 of the subject's display device 115 at various different exemplary steps of another embodiment of an eye test performed by the system illustrated in FIG. 1, and the possible appearance of the test patterns as they may be perceived by the test subject at some exemplary steps of the eye test.

In performing the flash test, the patient or test subject may be positioned before the screen 112 with the distance of the tested eye being preferably approximately 50 centimeters from the screen 112. Other different distances may however also be used depending, inter alia, on the dimensions of the screen 112, and on the size of the displayed test patterns.

The "flash test" method may begin by presenting to the patient or test subject one or more log-on screens, such as but not limited to the screen 300 schematically illustrated in FIG. 3. Other additional screens (not shown) may also be presented for entering other patient demographic data or the like. Once the patient identity has been established, screen 370 (FIG. 5A) may be presented to the patient.

A fixation target 372 is displayed on the screen 112. The fixation target 372 may be a circular pattern or may be any other suitably shaped pattern as disclosed in detail hereinabove for the fixation target 228 of FIG. 3. A cursor 373 may also be displayed on the screen 370. If the patient is trained to take the test, the trainer or test supervisor may explain to the patient that he or she should cover one eye (by hand or by using a suitable eye occluding device or patch), look at the screen 370 with the non-covered eye, and bring the cursor 373 to point at the fixation target 372.

Preferably, but not obligatorily, the movement of the cursor 373 may be restricted to the horizontal direction. For example, in accordance with one possible implementation of the method, the tip of the arrowhead-like pointing part 373A of the cursor 373 may be pointed upwards and it's movement may be restricted along an imaginary non-visible horizontal line (not shown) intersecting the fixation target 372. The patient may bring the cursor 373 to point at the fixation target 372 by using a mouse or any other suitable pointing device, as disclosed in detail hereinabove for the moving line method.

Similar to the fixation target 228 of FIG. 3, the fixation target 372 may be sized so that it is large enough to be seen by the patient or test subject but small enough so that bringing the cursor 373 to the fixation target 372 is a demanding task for the test subject. This causes the subject to fixate his vision on the fixation target 372. Upon bringing the cursor 373 to the fixation target 372, the subject may provide a suitable indication that he has positioned the cursor 373 to point at the fixation target 372. For example, the patient or test subject may provide the indication by clicking on a button of the mouse 125 or by depressing a predetermined key on the keyboard 120 (or by suitably using any other suitable pointing device known in the art or disclosed hereinabove). This patient input may serve as an indication or verification that visual fixation on the fixation target 372 has been achieved.

Figure 5A:
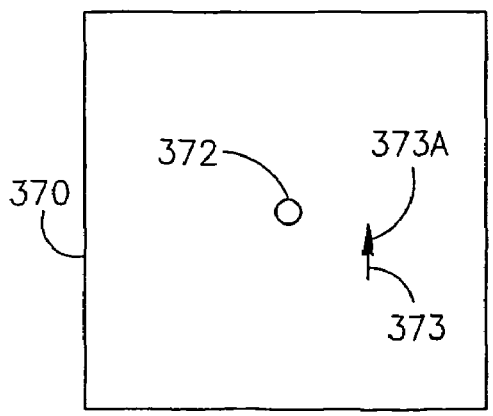
FIGS. 5A-5J are schematic diagrams illustrating patterns displayed at various different exemplary steps of another embodiment of an eye test performed by the system illustrated in FIG. 1, and the possible appearance of the test patterns as they may be perceived by the test subject at some exemplary steps of the eye test.
Figure 5B:
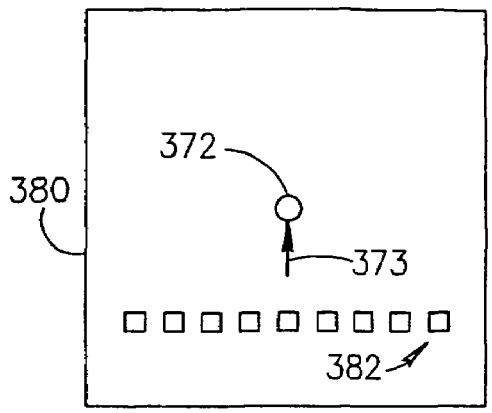

After the patient indicates fixation as disclosed hereinabove, a test pattern in the form of a segmented straight line 382 is presented to the patient (see screen 380 of FIG. 5B). It is noted that while the exemplary test pattern illustrated in FIG. 5B is a segmented straight line 382 as disclosed hereinabove for the moving line test method, other types of different test patterns (not shown) may however also be used. The segmented straight line 382 may be presented on the screen 112 immediately after the patient clicks the mouse 125 or may be presented after a delay. If a delay is used, the duration of the delay may preferably be in the range of approximately 0-200 milliseconds, but other higher values of the duration of the delay may also be used. The segmented straight line 382 may be displayed on the screen 112 for a short duration. Preferably, the duration of presentation of the test pattern (the line 382) on the screen 112 may be in the range of approximately 100-160 milliseconds. It was practically found that most patients perform the test well with the test pattern presentation duration in this range which enables to keep the duration of a test in the approximate range of 2-3 minutes (for a typical test including the presentation of 23 vertical segmented lines and 23 horizontal segmented lines).

It is noted that duration of presentation may also be shorter or longer. Typically, a duration of approximately 10-20 milliseconds may be on the threshold of observation for most patients. Thus, presentation duration values which are longer than 10-20 milliseconds may have to be used for most patients. The threshold of observation may however vary, inter alia, with the patient's age, visual acuity, or the like.

It is also noted that the test pattern presentation duration may also be longer than 160 milliseconds, but this may increase the overall test duration.

One advantage of the relatively short duration of the presentation of the test pattern (also referred to herein as "flashing" of the test pattern) may be that the eye/brain system of the patient may not have enough time to "fill-in" the distorted or missing or different parts of the perceived image of the test pattern, as it may do when the test pattern is static or is presented for a relatively long period of time. This may advantageously reduce or prevent such "filing-in" phenomena disclosed in detail hereinabove, which may decrease the probability of the patient not observing or not detecting (and therefore not reporting) a difference in the appearance of the perceived test pattern (as may often occur in the use of the Amsler test).

It may be further explained to the patient either before performing the test or while the test is being taken) that he is going to be presented with test patterns on the screen 112. The patient may, for example, be told that the presented test patterns are going to be segmented straight lines, and that the reference pattern against which he is to compare what he actually perceives on the screen 112 is a segmented straight line.

The patient may further be instructed that if he or she detects any difference between the perceived form of the presented test pattern or of one or more parts or portions thereof and the reference pattern (which is a straight segmented line in the non-limiting example illustrated in FIGS. 5A-5J), he or she is requested to indicate the approximate location of the part or parts which were perceived to differ from the reference pattern as is disclosed in detail hereinafter. For example, may be explained to the patient that one or more of the segments of the straight line may deviate from linearity or may appear to move, or may appear wavy, or may appear to bulge or to deviate or to be distorted such they are not perceived to be arranged as a straight line, and that other differences may also be observed such as, for example, a movement of one or more segments or parts of the perceived image of the test pattern relative to other parts or segments or portions of the perceived test pattern, or a dimming or brightening of some segments relative to the rest of the segments, or a change in the hue or color of some segments relative to the hue or color of other segments, or a fuzziness or blurring of one or more segments relative to the other segments, or that one or more segments or portions of the segmented straight line may appear to be missing, and that other differences may also be perceived.

Figure 5C:
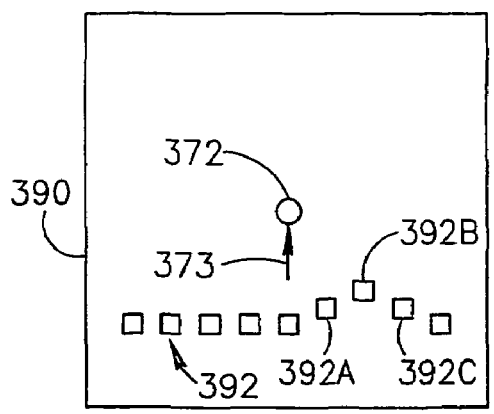

FIG. 5C schematically illustrates a screen 390 which is a representation of how the presented screen 380 (FIG. 5B) may be perceived by a patient having a retinal lesion while the patient's tested eye is fixated on the fixation target 372. The perceived image perceived by the patient may be a distorted segmented line 392 (FIG. 5C). In the perceived distorted line 392, the segments 392A, 392B, and 392C are perceived as shifted or distorted, or moving, or forming a bulge such that they are not arranged in a straight line. This may be due to the presence of a retinal lesion.

Figure 5D:
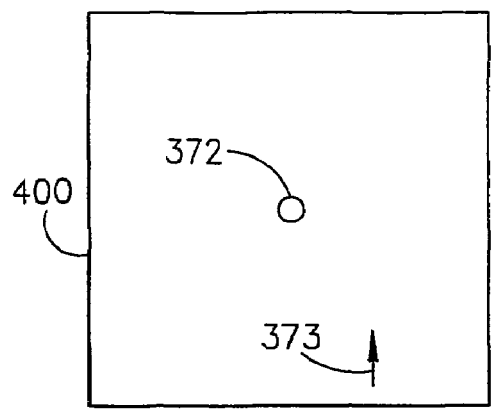
Figure 5E:
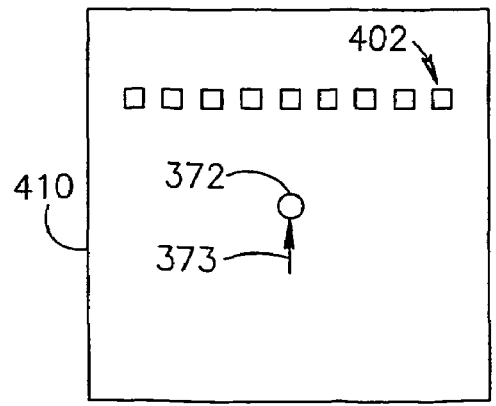

After the presentation of the test pattern is terminated, the test pattern 382 disappears from the screen 112 by terminating the displaying thereof on the screen 112. The patient may then indicate or mark the approximate location of the perceived region of difference or distortion on the perceived image. This marking or indicating may be performed, for example by the patient using the mouse 125 to move the cursor 373 to the region of the screen 112 where the difference was observed or detected. FIG. 5D illustrates the appearance of a screen 400 after the patient moved the cursor 373 to the approximate position on the screen at which the patient observed the distortion in the perceived image illustrated in FIG. 5C. This position roughly matches the region where the segments 392A, 392B, and 392C (of FIG. 5C) were perceived by the patient as shifted or distorted. After the positioning of the cursor 373 at the approximate position at which the difference or distortion was observed the patient may click a button on the mouse 125. The computer system 105 may thus determine from the position of the cursor 373 in screen 400 (FIG. 5D) the location on the test pattern at which a difference or distortion was observed or detected by the patient in the perceived image 392 of the test pattern 382 which was presented in screen 380 (of FIG. 5B). This location may be stored as data in the computer system 105.

It is noted that while in screens 370 and 380 (of FIGS. 5A and 5B, respectively) the movement of the tip of the arrowhead-like 373A of the cursor 373 was restricted along an imaginary non-visible horizontal line (not shown) intersecting the fixation target 372, after the termination of the presentation of the test pattern 382, the cursor is preferably not restricted and may be moved to any point on the screen 400. Alternatively, the moving of the cursor 373 may remain vertically restricted as disclosed hereinabove, in which case the patient may mark the location of the observed distortion or difference by moving the cursor 373 horizontally (not shown) until it reaches a location which is above or below the region at which the difference or distortion was observed on the perceived test pattern, (depending on whether the location of the appearance of the test pattern was below or above the fixation target 372, respectively).

The computer system 105 may thus store data representative of the location (or locations) marked by the patient. In accordance with one exemplary embodiment of the invention, the data may include the position of the test pattern 382 on the screen 380 and the position on the test pattern 382 which is equivalent to the horizontal position marked by the cursor 373 on the screen 400 (which is indicative of the location which was marked by the patient as the approximate region of the distortion perceived by the patient). Other different methods of storing the data may also be used as may be apparent to those skilled in the art.

It is noted that the computer 105 may also store other information or data associated with the presented test pattern. For example, the stored data may include, but is not limited to, the number of the test pattern (which may be indicative of the order of presentation of the particular test pattern within the test), the orientation of the test pattern (for example, vertical or horizontal, or the like), or any other data related to other parameters of the test pattern.

After the marked position of the distortion is stored, the patient may initiate the presentation of a new test pattern by repositioning the cursor 373 to point at the fixation target 372 and clicking a button on the mouse 125 as disclosed for screen 380 (of FIG. 5B) to indicate the achieving of fixation. This may cause the presentation of a new test pattern 402 as illustrated in the screen 410 of FIG. 5E. In this exemplary screen, the test pattern 402 is briefly presented at a new location on screen 410, different than the location of the test pattern 382 on screen 380 (FIG. 5B). The patient may perceive the presented test pattern 402 as a segmented straight line with no distortion (or no difference from the reference pattern) if there is no retinal lesion in the retinal region on which the image of the test pattern 402 is projected when the patient maintains visual fixates on the fixation target 372. The patient does not mark any position on the screen 410 since no distortion or difference from the reference pattern were observed by the patient. The patient may then proceed by visually fixating on the fixation target 372 and clicking on the mouse 125 to initiate the presenting of a new test pattern (not shown).

It is noted that in accordance with one embodiment of the invention, the cursor 373 may be automatically shifted to a new position away from the fixation target 372 following the termination of the presentation of the test pattern. This may be advantageous since it may force the patient to bring the cursor 373 again to point at the fixation target 372 which may ensure proper visual fixation before the presentation of each new test pattern. This however is not mandatory, because it may be possible to train the patient to perform visual fixation on the fixation target 372 prior to clicking the mouse to initiate the presentation of an additional test pattern, and because it may also be possible to independently monitor patient fixation by the presentation of artificially distorted test pattern as disclosed hereinabove and hereinafter.

In accordance with one embodiment of the invention, after a sufficient number of test patterns at appropriate locations have been presented to the patient to adequately map the desired field of vision with a desired resolution, the test may be terminated. In accordance with another embodiment of the invention, the test may further continue by changing the orientation of the presented test patterns such that a new sequence of test patterns is presented to the patient which test patterns are vertically oriented segmented straight line.

Figure 5F:
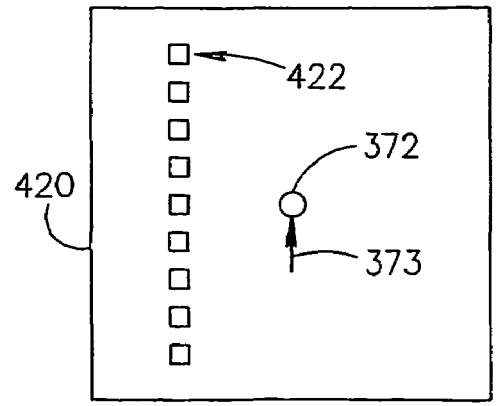

In screen 420 of FIG. 5F a vertically oriented test pattern 422 is illustrated. Preferably, but not necessarily, the shape, length and number of segments of the vertically oriented test pattern 422 may be similar to the shape, length and number of segments of the horizontally oriented test patterns previously presented to the patient (such as, for example, the horizontally oriented test pattern 382 of FIG. 5B). This, however is not mandatory, and the shape, or the length or the number of segments of the vertically oriented test patterns may be different than those of the horizontally oriented test patterns.

If the patient noticed no difference or distortion in the perceived pattern (not shown) of the test pattern 422 presented to the patient, the patient may re-fixate on the fixation target 372, and indicate visual fixation by clicking the mouse 125 to cause the presentation of a new (vertically oriented) test pattern.

Figure 5G:
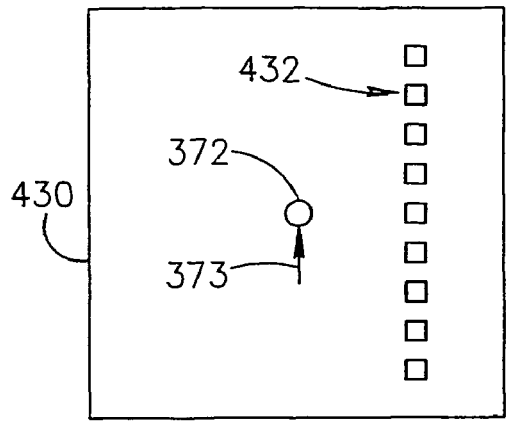

FIG. 5G illustrates an exemplary (vertically oriented) test pattern presented to the patient during a part of the test. The test pattern 432 is presented in a location of screen 430 as illustrated in FIG. 5G.

Figure 5H:
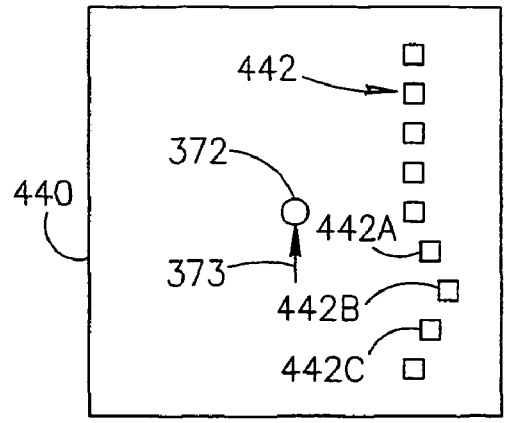

FIG. 5H schematically illustrates a screen 440 which is a representation of how the presented screen 430 (of FIG. 5G) may be perceived by the patient having a retinal lesion while the patient's tested eye is fixated on the fixation target 372. The perceived image perceived by the patient may be a distorted segmented line 442 (FIG. 5H). In the perceived distorted line 442, the segments 442A, 442B, and 442C are perceived as shifted or distorted, or forming a bulge such that they are not arranged in a straight line. This perceived distortion may possibly be due to the presence of the same retinal lesion which caused the distortion in the perceived image 392 (FIG. 5C) of the presented test pattern 382 of FIG. 5B. The distortion in the perceived image 442 may however also be due to the presence of another different retinal lesion.

Figure 5I:
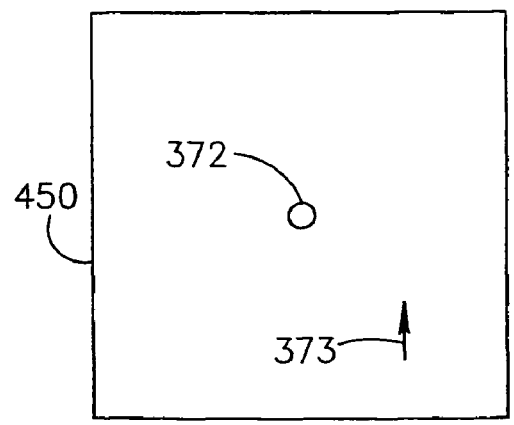

After the termination of the presentation of the test pattern 432 (FIG. 5G), the patient may mark the location of the perceived distortion-as illustrated in screen 450 of FIG. 5I by moving the cursor 373 to point at the approximate location of the distortion and clicking the mouse 125 which stores data representing the location of the observed distortion in the computer system 105, as disclosed hereinabove. Additional vertical test patterns at different locations may then be presented to the patient until the mapping of the retina using vertically oriented test patterns is completed at a desired resolution. Testing of the second eye of the patient may then be also performed by covering or occluding the already tested eye of the patient and repeating the same testing procedure for the uncovered non-tested eye.

The use of "Artificial Distortions" in the Flash Test Method

Preferably, in accordance with an embodiment of the invention, it may be possible to include intentional distortions in the test patterns presented in the flash test method disclosed hereinabove by presenting the patient with artificially distorted test patterns. The artificially distorted patterns may include, inter alia, any of the types of distortions included in the artificially distorted test patterns disclosed hereinabove for the "moving line" test method (for one, non-limiting example of such an artificial distortion see screen 360 of FIG. 3). Thus, some of the test patterns presented to the patient may be artificially distorted, as disclosed hereinabove. For example, one out of three (approximately 30%) test patterns presented to the patient may be an artificially distorted pattern. Other different ratios of artificially distorted to non-distorted test patterns may also be used.

Among the advantages of presenting artificially distorted test patterns is, that this may train the patient in what may be the appearance of a perceived distortion if a retinal lesion is present. This training may improve the patient's ability to detect and report such distortions if such a distortion or similar distortions appear in the perceived image following the presentation of a non-distorted test pattern to the patient.

Another advantage, as explained hereinabove, may be the possibility to assess the degree of attention of the patient, and the reliability of the test results. Thus, if the patient fails to reliably report the presence and the location of the distortions displayed in the artificially distorted test patterns, this may be used as an indication of possible lack of attention of the patient, due to fatigue or other reasons, or this may also be used as an indication that something is wrong with the test presentation or with the test results, or with the patient's ability to visually perceive the test patterns, in which case the test results may be ignored (such as, for example, when the test is performed by the patient alone without the supervision of a trainer or supervisor). If a trainer or supervisor is present near the patient and such a testing non-reliability is reported, for example by an appropriate error message (not shown) appearing on the screen 112 or otherwise, the supervisor or trainer may stop the test (and may cancel the record of the test results if appropriate) and may try to find and rectify the reasons for the patient's failing to reliably report the presence and location of the distortions.

For example, the trainer or supervisor may check if the patient's tested eye is positioned at the appropriate distance from the screen 112, or if the patient is fatigued or not paying attention to the test patterns or not properly fixating his vision at the fixation target 373, or the like. Such problems may be thus rectified and another test may be initiated if desired.

Figure 5J:
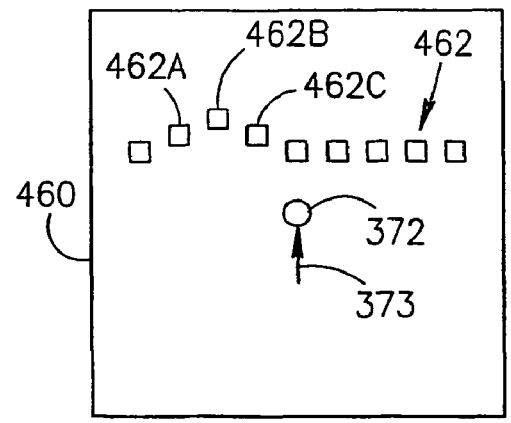

FIG. 5J illustrates one possible form of an artificially distorted test pattern which may be possibly used in the example of the flash testing method illustrated in FIGS. 5A-5I. In screen 460 of FIG. 5J an artificially distorted line 462 is illustrated as presented to the patient on the screen 112. The segments 462A, 462B and 462C of the presented line 462 are positioned and oriented such that they are not aligned (or mis-aligned) with the remaining segments of the test pattern 462. In other words, while the remaining segments of the test pattern 462 are aligned to form a straight line, the segments 462A, 462B and 462C form a bulge or curved part or wavy part of the test pattern 462. The test pattern 462 (which may be presented on the screen 112 of the display device 115) is thus an artificially intentionally distorted test pattern. Thus, when the artificially distorted test pattern 462 is presented to the patient who is visually fixated on the fixation target 373, the patient may perceive the distortion as a deviation of the segments 462A, 462B and 462C from the expected reference pattern of a straight segmented line.

The patient may then proceed to indicate or mark the approximate location of the perceived distortion by bringing the cursor 373 to the approximate location of the perceived distortion and clicking the mouse 125 as disclosed in detail hereinabove. For example, the patient may position the cursor 373 at the approximate position on the screen 112 at which the patient perceived the image of the segment 462B while the test pattern 462 was presented (flashed) on the display device 115, and may click on the mouse 125 to input and store the approximate location of the perceived distortion in the test pattern 462. The location reported by the patient may be compared to the known location of the distortion in the presented artificially distorted test pattern 462.

It is noted that if the patient detects or observes two or more spatially distinct distortions or abnormalities along the presented test pattern, the patient may mark the approximate location of all such detected distortions or visual abnormalities by suitably bringing the cursor 373 to the location at which the additional distortion or visual abnormality was observed and clicking the mouse 125. Thus, the data stored for a test pattern may include the location on the test pattern of more than one detected distortion or visual abnormality.

Typically, about a third (approximately 30%) of the test patterns presented to the patient may be artificially distorted test patterns. The percentage of the artificially distorted test pattern out of all the test patterns presented to the patient may however vary, depending, inter alia, on previous knowledge of the test performance of the same patient in past tests, or on other considerations. Additionally, the artificially distorted test patterns may be randomly or pseudo-randomly distributed among the rest of the test patterns during a test so that the patient cannot predict the time of presentation of the artificially distorted test patterns by learning the sequence of presentation of these signals.

It is noted that generally vertically oriented artificially distorted test patterns (not shown) may also be presented to the patient (the word "generally" refers to the vertical orientation of the majority of the non-distorted segments which are aligned along an imaginary straight line, even if some of the segments may be horizontally displaced in the region of the artificial distortion).

Typically, the location of the distorted portion or segments on the artificially distorted test pattern may be randomly or pseudo-randomly changed or altered in different presentations of artificially distorted test patterns performed within a test. Such random alteration of the location of the artificial distortion along the test pattern is advantageous because it makes it more difficult for a patient to cheat (either intentionally or non-intentionally) in comparison with a situation in which the distortion is always presented at a fixed location on the test pattern.

If the patient fails to reliably identify and report the presence and the location of the distortion presented in a predetermined percentage of the artificially distorted test patterns which were presented to the patient in a test, the test results may be ignored or discarded as unreliable. For example, in accordance with one non-limiting exemplary embodiment of the method of the present invention, if the patient did not report reliably the presence and the location of the artificial distortion (or another test pattern modification used in the test) in 20% of the total number of artificially distorted test patterns presented within a test, the test results may be ignored or discarded as unreliable.

Thus, in accordance with such an exemplary (non-limiting) test reliability criterion, if in a test the patient was presented with 60 test patterns, and 20 test patterns out of the 60 test patterns were artificially distorted (or otherwise modified) test patterns, the patient has to reliably report the presence and location of the artificial distortion (or of any other test pattern modification which was used in the modified test pattern) in at least four out of the twenty presented artificially distorted test patterns in order for the test results to satisfy the reliability criterion.

It is noted that in accordance with the exemplary embodiment of the reliability criterion disclosed hereinabove, it is not enough for the patient to just identify the presence of the distortion or modification which was artificially introduced in the presented test pattern, but the patient has to correctly mark the position of the artificial distortion (or other test pattern modification) in the test pattern within a specified predefined positioning accuracy criterion.

Typically, in accordance with one possible exemplary embodiment of the present invention, the position marked by the patient as the position of the distortion (or other modification, if used) has to fall within a 1.5° cone angle on each side of the center point of the artificial distortion in to satisfy the position accuracy criterion, but other different cone angles may also be used.

Figure 6:
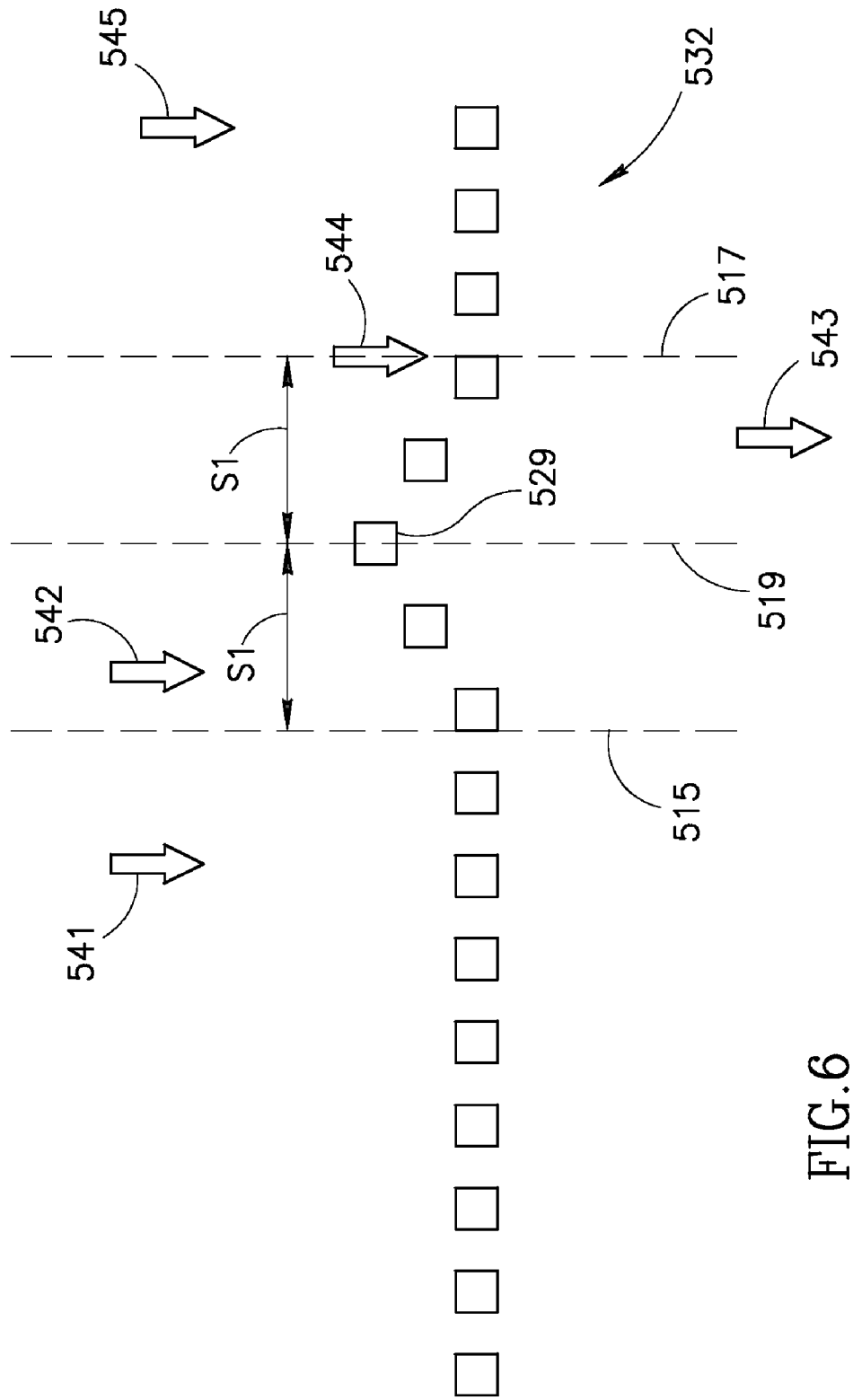
FIG. 6 is a schematic diagram useful in understanding an exemplary positioning accuracy criterion which may be used in the eye testing method, in accordance with one exemplary embodiment of the present invention.

Reference is now made to FIG. 6 which is a schematic diagram useful in understanding an exemplary positioning accuracy criterion which may be used in the eye testing method, in accordance with one exemplary embodiment of the present invention.

The segmented line 532 schematically represents an artificially distorted horizontal line 532 as presented (flashed) on the screen 112 to the subject 100. The segment 529 represents the approximated center of the artificial distortion of the line 532 as presented on the screen 112. The tips of the arrows 541, 542, 543, 544 and 545, schematically represent some possible locations where a subject may potentially mark the position of the approximate the center of the perceived distortion. It is noted that the points clicked on by the subject (which are schematically indicated by the points at the tip of the arrows 541, 542, 543, 544 and 545) need not be on the exact line 532 as perceived by the patient and may be either on or below or above the position on the screen 112 at which the line 532 was briefly presented. The dashed line 519 schematically represents an imaginary vertical line passing through the center of the segment 529 and the dashed lines 515 and 517 schematically represent two imaginary lines parallel to the vertical line 519 and extending to the end (not shown) of the screen 112. The distance S1 between each of the imaginary lines 515 and 517 and the imaginary line 519 is equivalent to a cone angle of 1.50° of the visual field of the subject ( when the subject's eye is positioned 50 centimeters from the screen 112.

If the position marked by the subject 100 falls on one of the imaginary lines 515 and 517 or falls anywhere between the two lines 515 and 517, the marked position passes (satisfies) the positioning accuracy criterion and the marked position is deemd to be accurate. If the position marked by the subject 100 falls on the region on the left side of the imaginary line 515 or on the screen region on the right of the imaginary line 517, the marked position does not satisfy the positioning accuracy criterion and the marked position is deems to be inaccurate. Thus, for example, the marked positions represented by the tip of the arrows 541 and 545 do not satisfy the positioning accuracy criterion while the marked positions represented by the tip of the arrows 542, 543 and 544 satisfy the positioning accuracy criterion.

It is noted that other different types of positioning accuracy criteria may also be used. For example the cone angle represented by the distance S1 may have other values which are smaller or larger than 1.50°. Furthermore, if the test patterns used are slanted lines, other positioning accuracy criteria may need to be established and used.

It is further noted that the satisfying of the of positioning accuracy criterion may be computed or evaluated by the computer 105 or by any other suitable computing device, using any suitable computational algorithm as is known in the art.

Analysis of Test Results

The results of the tests performed as disclosed hereinabove may need to be suitably analyzed in order to provide the patient with proper instructions, and possibly his health care provider with a report of the test results. In the case were the patient has been trained to perform the test at home using a desk-top computer or a portable computer (a laptop computer) or the like, if a possible retinal lesion is detected in the test, the patient may be preferably provided with an output which may instruct the patient to promptly visit his ophtalmologist or an eye clinic for a thorough eye examination in order to check the existence of the suspected lesion. If upon this eye examination a lesion is verified, proper therapeutic treatment may be timely administered to the patient, which may substantially improve patient's prognosis due to early detection of the lesion. If no lesion is detected or suspected, the patient may be informed after the test is finished that the results are negative (no lesion is suspected).

Theoretically, if a single occurrence of a perceived distortion of a test pattern is reported or marked by the subject after a non-distorted test pattern is presented to the patient, the patient may be diagnosed as positive and the system may recommend or instruct the patient to visit an ophtalmologist for further eye examination. Such a simple diagnostic criterion may, however, result in a relatively large percentage of false positive diagnoses. This is because many patients may report a distortion in a certain percentage of the presented non-distorted test patterns. Thus, such a simple diagnostic criterion may not be widely applicable to all patients and may possibly be used only for certain subpopulation of patients (such as for example in very high risk patients in which it may be decided that a high percentage of false positive diagnoses is tolerable).

For most patient, however, other diagnostic criteria may have to be used for reducing the probability of false positive diagnosis.

In accordance with one possible embodiment of the invention, In order to establish if one or more visual disturbance was reliably detected, the data collected and stored in the test is processed as follows.

The data stored for all the non distorted test patterns are checked to see if any segment or component or portion was marked by the patient on any of the test patterns presented in the test. If such a marked segment or component or portion is found, the data for other test patterns is checked for the presence and location of marked segments in other different test patterns. While the finding of a single marked location in a single test pattern may be regarded as an indication of a suspected retinal lesion or retinal abnormality, such a single marked location may have been erroneously marked. It is therefore preferred to corroborate such a result by checking the data obtained for other different test patterns to find out if another location was marked on another test pattern. If two locations were indeed marked by the subject in two different test patterns it may be checked or computed if these two locations satisfy a proximity criterion.

Figure 7A:
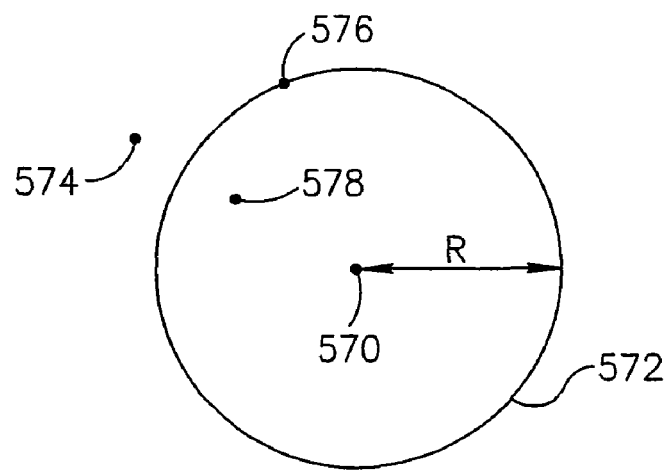
FIGS. 7A and 7B are schematic diagrams useful in understanding exemplary diagnostic criteria which may be used in exemplary embodiments of the present invention.
Figure 7B:
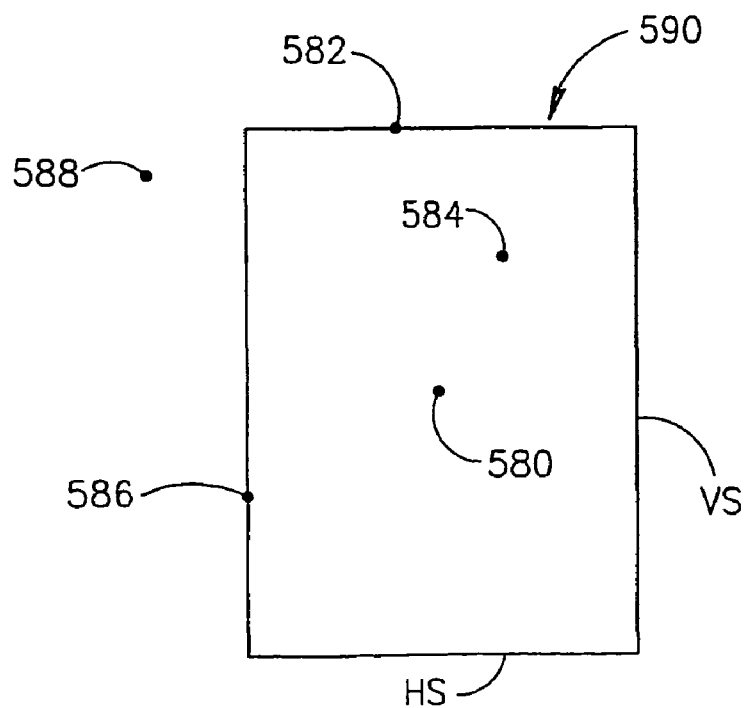

Reference is now made to FIGS. 7A and 7B which are schematic diagrams useful in understanding exemplary diagnostic criteria which may be used in exemplary embodiments of the present invention.

It is noted that the locations of the distortions marked and stored in the computer 105 as disclosed hereinabove may be normalized since they are all known relative to the fixation target. In other words, a correction may be computed to compensate for the movement of the fixation target on the screen 112. Therefore, the coordinates of the marked locations may be normalized relative to the fixation target (if the fixation target moves on the screen 112 as is the case in the moving line test). In this way all the marked points maybe related to each other for performing the computations of the diagnostic criteria. In the flash test there is no need for normalization since the fixation point does not change its position on the screen 112, and therefore the locations (coordinates) of the marked locations of the distortions or modifications may be used directly without normalization.

Different proximity criteria were used for different combinations of test patterns. The computation is performed on pairs of marked locations in two. If the pair of marked locations came from test patterns which are orthogonal to each other (such as for example a horizontal straight segmented line and a vertical straight segmented line) The proximity criterion is satisfied if the distance between the two marked locations is equal to or smaller than a cone angle of 3° (three degrees) assuming that the subject's eye was at a distance of 50 centimeters from the screen 112 during the test.

If the point 570 of FIG. 7A schematically represents the position of a first location marked by the subject in response to the presentation of a first test pattern. The circle 572 has a radius R which is equivalent to a cone angle of 3° (three degrees) assuming that the subject's eye was at a distance of 50 centimeters from the screen 112 during the test. If a another point which represents the location marked by the subject on another test pattern orthogonal to the first test pattern falls on or within the circumference of the circle 572 the proximity criterion (for pairs of orthogonal test patterns) is met indicating the presence of a retinal lesion. If the other point falls outside of the circumference of the circle 572, the proximity criterion is not met. For example, each point of the points 576 and 578 meets the proximity criterion with respect to the point 570, while the point 574 does not meet the proximity criterion.

It is noted that if the distance between the tested eye and the screen 112 is different than 50 centimeter, the proximity criterion may need to be changed by changing the value of the radius R.

If the two points being checked come from location marked on test patterns that are parallel (for example, two differently located straight segmented lines which are parallel, another proximity criterion is used. If the point 580 of FIG. 7B schematically represents the position of a first location marked by the subject in response to the presentation of a first test pattern. A rectangle 590 surrounding the point 580 has a horizontal side HS which is equivalent to a cone angle of 4° (four degrees) and a vertical side VS which is equivalent to a cone angle of 6° (six degrees) assuming that the subject's eye was at a distance of 50 centimeters from the screen 112 during the test. The point 580 is disposed at the geametrical center of the rectangle 590. If another point which represents the location marked by the subject on another test pattern parallel to the first test pattern falls on or within the circumference of the rectangle 590, the proximity criterion (for parallel test patterns) is met indicating the presence of a retinal lesion. If the other point falls outside of the circumference of the rectangle 590, the proximity criterion is not met. For example, each point of the points 582, 584, and 576 meets the proximity criterion with respect to the point 580, while the point 588 does not meet the proximity criterion.

It is noted that the proximity criteria disclosed hereinabove were empirically determined and that many other different types of criteria may be used, depending, inter alia, on the purpose of the test, the needed accuracy, the desired level of false positive diagnosis, and the particular group of patients for which the test needs to be applied. Thus, the proximity criteria indicated above are given by way of example only and other proximity criteria may be applied which are all within the scope of the invention.

It is further noted that when the test includes test patterns with artificial distortions, any locations which are marked by the subject which are within 3° (three degrees) on each side of the center of the artificial distortion are removed from the data prior to performing the calculations for checking any of the proximity criteria to prevent spurious positive results. If the size and shape of the artificial distortion is changed, a different distance from the center may be used for removing data which is due to the presence of the artificial distortion.

Figure 8:
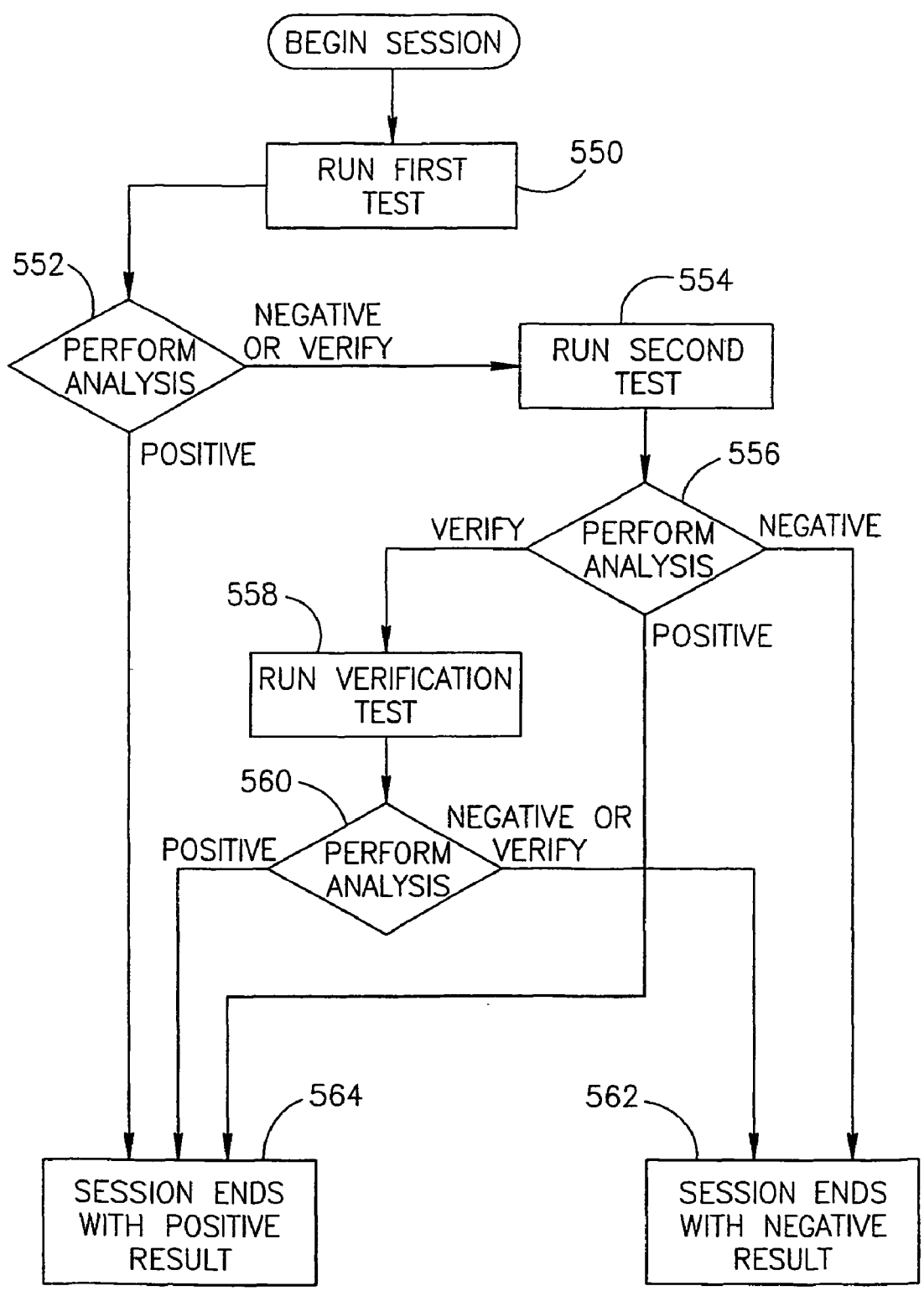
FIG. 8 is a schematic flow diagram useful in understanding a method for performing a test session and analyzing the results of the test session, in accordance with one possible embodiment of the present invention.

FIG. 8 is a schematic flow diagram useful in understanding a method for performing a test session and analyzing the results of the test session, in accordance with one possible embodiment of the present invention.

A test session may include one or more tests and begins by the patient performing a first test (step 550). The tests may be a moving line test or a flash test but in one session all tests are of the same type. After the first test is completed, the data is analyzed (step 552). The analysis may be performed using the proximity criteria as disclosed hereinabove and may result in any of three types of analysis results as follows:

1) a positive result is generated if a retinal lesion is found from the results of the first test by having at least two marked locations in two separate test patterns which meet the proximity criteria disclosed hereinabove.

2) a negative result is generated if the patient did not mark any location in any of the test patterns presented in the test.

3) a verify result is generated is the patient selected and marked locations on one or more test patterns presented during the test, but the marked locations did not meet the proximity criteria.

If the results of the analysis of step 552 generate a positive result, the session ends with a positive result (step 564) indicating that a lesion has been detected, and the session is terminated.

If the results of the analysis of step 552 generate a negative or a verify result, a second test is run (step 554). The second test is a repetition of the first test. The results of the second test are analyzed (step 556) according to the same method as in the analysis of step 552 except that the analysis is run on the pooled results of the firs and the second test.

If the results of the analysis of step 556 generate a positive result, the session ends with a positive result (step 564) indicating that a lesion has been detected, and the session is terminated.

If the results of the analysis of step 556 generate a negative result The session ends in a negative result and is terminated (step 562). If the results of the analysis of step 556 generate a verify result a verification test is run (step 558). The verification test may be different than the first test and the second test in that it does not present to the patient the full complement of the test patterns which are normally included in the first and the second test, but presents to the patient only test patterns which were previously marked by the patient in the pooled results of the first and the second tests. Additionally, while the first and second tests may include artificially distorted test patterns, preferably, the verification test does not include artificially distorted test patterns.

After the verification test is performed an analysis is performed on the pooled results of the first test, the second test and the verification test (step 560).

If the results of the analysis of step 560 generate a positive result, the session ends with a positive result (step 564) indicating that a lesion has been detected, and the session is terminated.

If the results of the analysis of step 560 generate a negative or a verify result, the session ends with a negative result (step 562) and the session terminates.

Experimental Results

Figure 9:
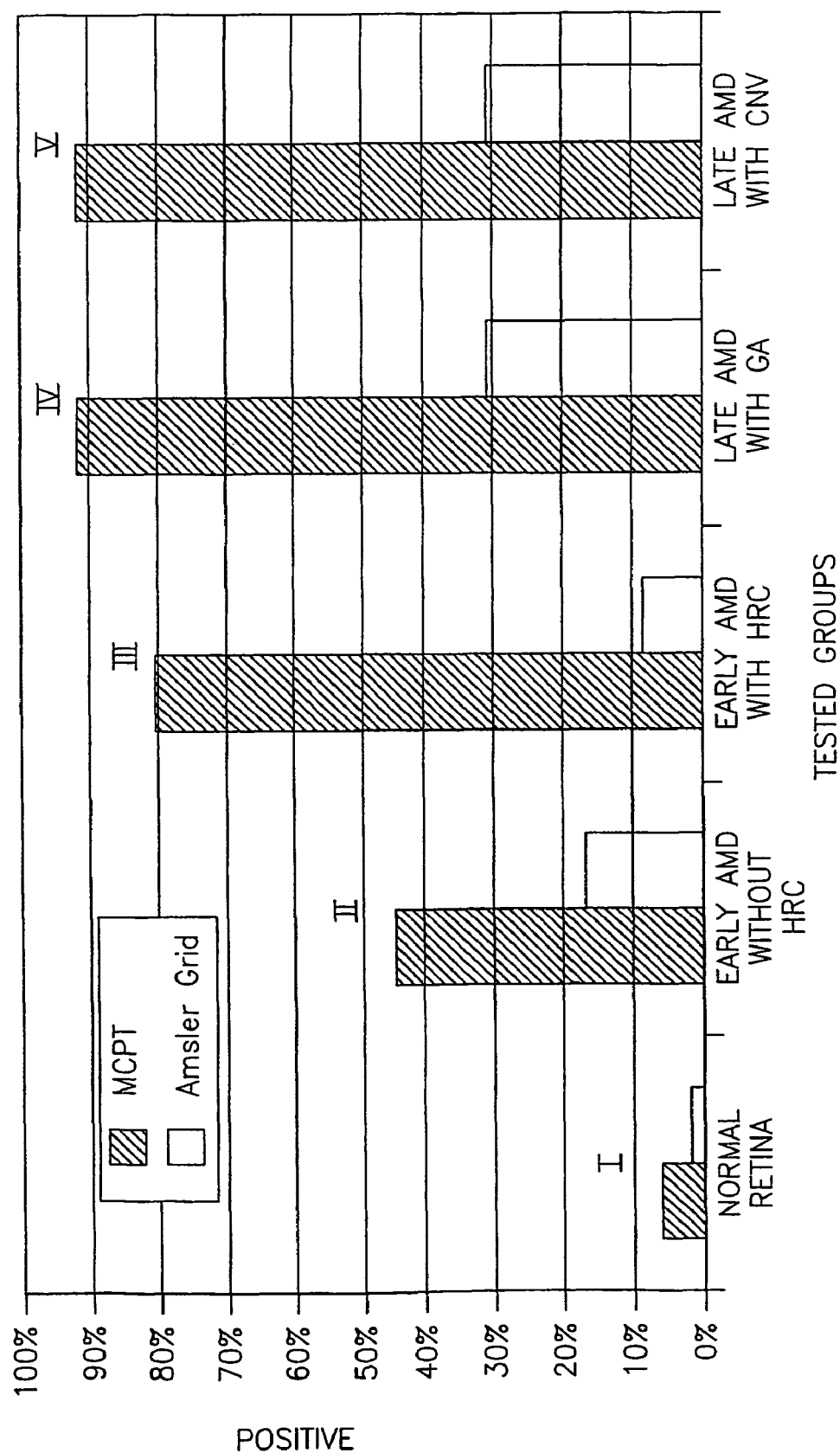
FIG. 9 which is a bar graph representing experimental results comparing the performance of the standard Amsler grid test with the performance of the eye test of the present invention.

Reference is now made to FIG. 9 which is a bar graph representing experimental results comparing the performance of the standard Amsler grid test with the performance of the eye test of the present invention.

The bar graph of FIG. 9 represents the results of testing performed on 108 eyes of patients with clinically diagnosed forms of AMD and on a group of control patients which had a normal retina (the control group).

The test was performed using the flash method as disclosed hereinabove.

The test patterns used were 23 vertical segmented straight lines and 23 horizontal straight segmented lines, each line spanning a 14° cone angle at a distance of 50 centimeters of the eye from the screen 112. The segments were rectangular white segments on a black background, each segment spanning 0.2°×0.2 cone angle. The segments of each line were separated from each other by a cone angle of 0.6°

The results of the control group are represented in the bar pair labeled I (Normal retina).

The group with 108 patient included four subgroups. The first subgroup (labeled 11) included 18 patients clinically diagnosed as having early AMD without high-risk characteristics (HRC) as in known in the art. Of this group the MCPT test resulted in a positive diagnosis in The third subgroup (labeled III) included 35 patients clinically diagnosed as having early AMD with high-risk characteristics (HRC) as in known in the art.

The fourth subgroup (labeled IV) included 23 patients clinically diagnosed as having late AMD with geographic atrophy (GA) as in known in the art.

The fifth subgroup (labeled V) included 32 patients clinically diagnosed as having choroidal neovascularization (CNV) as in known in the art.

The results of the MCPT for the subgroups are represented by the hatched bar of each bar pair and the results of the standard Amsler grid test are represented by the unfilled bar of each bar pair. The hight of the bars represents the percent of the patients in each relevant group which was diagnosed as positive in the test (Amsler test or MCPT test)

It can be seen that for subgroups II, III, IV, and V the MCPT test resulted in a significantly higher percentage of patients being positively diagnosed, as compared to the percentage of the patient diagnosed positive when the Amsler grid test was applied to the same group.

In the normal retina group (the control group I), the difference observed between the percentages of individuals showing positive diagnosis in the MCPT and Amsler grid test was not significant.

Testing System Configurations

It is noted that the testing systems and data analysis methods disclosed hereinabove may be implemented in different device and system configuration.

In accordance with one possible configuration of the system, the system may be implemented on a computer used at the patient's home. Such a computer may or may not be connectable to a network as disclosed in detail hereinabove. A software program may be installed on a commercially available desktop computer, or portable computer or any other suitable type of computer. The computer may be preferably connectable to a network for communicating the test results to a suitable server. Such a system may have the advantages of being inexpensive, simple to operate, and being operable at the patient's home.

In accordance with another configuration of the test system, the system may be meant for use at an eye clinic or at an ophtalmologists office. Such a system may be implemented on a powerful computer station or workstation and may also provide the ophtalmologist or other eye expert with more advanced data analysis and possibly graphical reports of the test results. Such reports may advantageously provide data about the possible location of the retinal lesion(s), an indication of the lesion size or magnitude, and may possibly include a more detailed report showing the history of test results of the tested patient.

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

It is noted that while the non-limiting examples of the testing system disclosed hereinabove and illustrated in FIG. 1 include a display device on the surface of which the various test patterns and the fixation target are presented to the subject, other types of systems for administering the test to the subject may be used which do not include a screen or surface. For example, in accordance with another embodiment of the present invention the test patterns and fixation target(s) may be presented to the subject by using an optical system (not shown) similar to a scanning laser ophtalmoscope (SLO).

Figure 10:
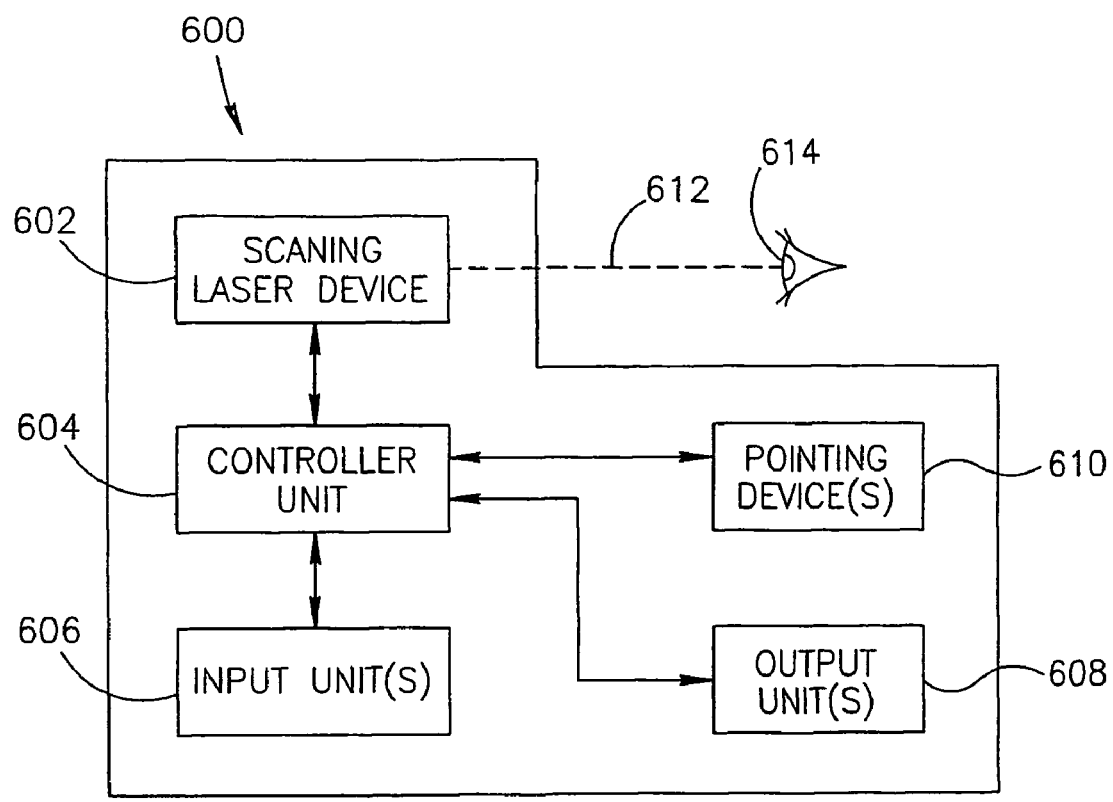
FIG. 10 is a schematic diagram illustrating a system including a scanning laser device or another eye scanning device usable for carrying out an eye test according to another preferred embodiment of the invention.

Reference is now made to FIG. 10 which is a schematic diagram illustrating a system including a scanning laser device usable for carrying out an eye test according to another preferred embodiment of the invention.

In the system 600, the images of the test patterns and fixation target(s), and possibly the log-on screen(s) may be directly projected on the retina of an eye 614 of the test subject (not shown) by suitably directing a laser beam 612 (schematically represented by the dashed line labeled 612) through the pupil of the tested eye 614 and by suitably scanning the laser beam 614 across the retinal surface to form projected images of the test patterns and/or fixation target(s) at specified locations on the retinal surface. The system 600 may include a scanning laser device 602. The scanning laser device 602 may be a scanning laser ophtalmoscope (SLO) device as is known in the art. Or any other device capable of controllably scanning a beam of coherent or non-coherent light across the retina of an eye. The scanning laser device 602 may be suitably coupled to a controller unit 604 or to a computer (not shown) for controlling the operation of the scanning laser device 602. The controller unit 604 may also be a computer such as a workstation, or mainframe, or laptop computer or a hand held or other portable computing device, or a personal computer or any other type of computing device known in the art. The controller unit 604 may be coupled to suitable pointing device(s) 610. The pointing device(s) 610 may be a mouse (not shown), and/or keyboard connected to a computer or may be any other suitable pointing device or devices as disclosed hereinabove or as known in the art. The system 600 may also include one or more output unit(s) 608, such as, but not limited to a display, a printer unit, or any other suitable output device for enabling interaction of a user with the system 600 and/or for producing hard copy output of test results or the like. The output unit(s) 608 may be suitably coupled or connected to the controller unit 604.

In operation the system 600 may be used for applying any of the tests disclosed hereinabove but instead of showing the test pattern, and the fixation targets on a screen 112 of a display device 115, the images of the test patterns and the fixation target(s) may be directly projected onto the retina of the tested eye 614 by the scanning laser device 602 by suitably scanning the laser beam 612 on the retina of the eye 614. The laser beam 612 may also be used to project an image of a cursor (similar to the cursor 225 of FIG. 3) directly on the retina of the eye. The movement of such a projected cursor may be controlled by the one or more of the pointing devices 610, such as but not limited to a mouse (not shown). Thus, the system 600 may be used to administer to a patient any of the tests disclosed hereinabove (including but not limited to the moving line test and the flash test) and to record and stor the responses of the patient including but not limited to the marking of parts or portions or segments at which distortions or modifications as disclosed hereinabove were perceived and marked by the patient. The system 600 may also process the test results using any of the methods and test criteria disclosed hereinabove to produce a positive or negative diagnosis. The system 600 may also be suitably connected to a communication network (such as, but not limited to the communication network 130 of FIG. 1) and may communicate with other devices or computers, or the like over the communication network.

It is noted that the laser scanning device 602 may be replaced or substituted with other scanning devices (not shown) known in the art which are capable of directing a narrow light beam having a suitably narrow beam cross-sectional area onto an eye and scanning the beam controllably across the retina. The light beam need not be a laser beam but may be any beam of non-coherent light which may be suitably scanned across a retina with sufficient speed and resolution.

It is noted that the construction and operation of laser scanning ophtalmoscopy devices is well known in the art, is not the subject matter of the present invention and is therefore not described in detail herein.

It will be appreciated that the preferred embodiments disclosed hereinabove and illustrated in the drawings are given by way of example only and that many variations and modifications of the present invention may be made which are within the scope and spirit of the present invention.

The invention claimed is:

1. A method for detecting eye disease in an individual, the method comprising the steps of:
   (a) projecting a first pattern on a first location on the retina of an eye of said individual;
   (b) fixating the individual's vision on a fixation target projected on said retina at or about said first location;
   (c) hiding at least a portion of said first pattern;
   (d) projecting a second pattern on a second location of said retina to allow the individual to form a perceived image of said second pattern;
   (e) receiving from said individual input indicative of a difference in at least one localized part of said perceived image as compared to a predefined reference pattern, if said individual detected said difference;
   (f) repeating steps (a) to (e) a number of times to obtain a plurality of data; and
   (g) determining whether the individual has an eye disease based on said plurality of data.

2. The method according to claim 1 wherein said fixation target is part of said first pattern.

3. The method according to claim 1 wherein said hiding is performed in response to said fixating.

4. The method according to claim 1 wherein the steps (a) to (g) are performed in the order recited in claim 1.

5. The method according to claim 1 wherein said determining of step (g) comprises outputting a positive result indicative of the presence of a retinal or choroidal lesion in said eye of said individual if said difference is detected in at least one repetition of step (e).

6. The method according to claim 1 wherein said second pattern is selected from said predefined reference pattern and a modified form of said reference pattern.

7. The method according to claim 6 wherein said modified form of said reference pattern is selected from,
  a pattern in which at least one portion of the pattern is distorted in comparison with said reference pattern,
  a pattern in which an optical property of at least one part of the pattern is different than the corresponding optical property of the remaining part of said pattern,
  a pattern in which at least one portion of the pattern is visually different in comparison with the corresponding portion of said reference pattern,
  a pattern in which at least one portion of the pattern is missing in comparison with said reference pattern,
  a pattern in which at least one part of the pattern is blurred in comparison with the remaining part of said pattern.

8. The method according to claim 7 wherein said optical property is selected from the group consisting of the color of said part, the hue of said part, and the brightness of said part.

9. The method according to claim 1 wherein said second pattern and the predefined reference pattern are substantially identical, and wherein said perceived image and said predefined reference pattern are not identical.

10. The method according to claim 1 wherein said second pattern and the predefined reference pattern are not identical.

11. The method according to claim 1 wherein the second pattern and the reference pattern are substantially identical, an eye disease being detected when the perceived image and the predefined reference pattern are not identical.

12. The method according to claim 11 wherein the reference pattern is a segmented straight line comprising a plurality of segments, and step (e) comprises marking at least one position within said second pattern representing the approximate position of a segment in the second pattern perceived by the individual to be misaligned relative to other segments, or blurred relative to other segments, or visually different than the other segments, or having an optical property different than the optical property of other segments of said second pattern, or absent from said second test pattern.

13. The method according to claim 1 wherein the second pattern and the reference pattern are not identical.

14. The method according to claim 13 wherein the reference pattern is a straight segmented line comprising a plurality of segments, the second pattern is obtained from the reference pattern by misaligning at least one segment relative to other segments of the segmented line, bluffing of at least one segment relative to other segments of the segmented line, altering an optical property of at least one segment of the segmented line, or removing of at least one segment of the segmented line, and wherein step (e) comprises indicating a region in the vicinity of a segment of said second pattern perceived by the individual to be misaligned relative to other segments of said second pattern, to be blurred relative to other segments of said second pattern, to have optical properties different than the optical properties of other segments of said second pattern, or to be absent in said second pattern, respectively.

15. The method according to claim 13 wherein the second pattern is similar to an image perceived by an individual having an eye disease when said reference pattern is projected onto a diseased region of the retina of an eye of said individual having an eye disease.

16. The method according to claim 13 wherein the second pattern is similar to the image perceived by an individual with eye disease when the predefined reference pattern is projected onto a location of the eye having a retinal or choroidal lesion.

17. The method according to claim 13 wherein the reference pattern comprises a plurality of components and the second pattern is obtained by a modification of the reference pattern, the modification is selected from the group consisting of,
  displacing at least one component of the reference pattern,
  removing at least one component of the reference pattern,
  blurring at least one component of the reference pattern;
  changing a visually perceivable characteristic of at least one component of said reference pattern, and
  changing an optical property of at least one component of the reference pattern.

18. The method according to claim 1 wherein the reference pattern and the second pattern comprise one or more lines.

19. The method according to claim 18 wherein the reference pattern and the second pattern comprise two or more parallel lines.

20. The method according to claim 19 wherein the spacing between at least one pair of adjacent parallel lines of said two or more parallel lines is from about 10 to about 600 minutes arc.

21. The method according to claim 18 wherein one or more of said lines is a segmented line comprising a plurality of segments.

22. The method according to claim 21 wherein the gaps between said segments are between 0 and 300 minutes arc in length, and each segment of said plurality segments has a height and a width between 1 and 120 minutes arc.

23. The method according to claim 1 wherein the reference pattern comprises a plurality of identical components.

24. The method according to claim 1 wherein the reference pattern comprises a plurality of components at least two components of said plurality of components are not identical.

25. The method according to claim 1 wherein the second pattern is selected from a rotated form of said reference pattern, a translated form of said reference pattern, and a translated and rotated form of the reference pattern.

26. The method according to claim 1 wherein said difference is selected from the group consisting of:
  at least one portion of the reference pattern that is displaced in the perceived image;
  at least one portion of the reference pattern that is missing in the perceived image;
  at least one portion of the reference pattern that is blurred in the perceived image; and
  at least one portion of the reference pattern having an altered optical property in the perceived image.

27. The method according to claim 1 wherein said individual indicates the position of said at least one difference within said perceived image.

28. The method according to claim 1 wherein said difference is a transient difference.

29. The method according to claim 1 wherein the projecting of said first pattern, said fixation target and said second pattern on said retina is performed by displaying said first pattern, said fixation target and said second pattern to said individual on a display device.

30. The method according to claim 29 wherein at least some data of said plurality of data is transmitted over a communication network to a processor and stored in a memory.

31. The method according to claim 30 wherein the communication network is a computer network such as local area network, a wide area network, the Internet, an intranet, a LAN, a WAN or a PAN.

32. The method according to claim 30 wherein one or more comparisons are transmitted over the communication network in real time.

33. The method according to claim 30 further comprising a step of transmitting over the communication network times at which the method is performed by the individual and storing the times in a memory.

34. The method according to claim 33 further comprising a step of sending a reminder to the individual to perform the method if the individual fails to perform the method as instructed by a health care provider.

35. The method according to claim 33, further comprising a step of transmitting over the communication network in real time to a health care provider of results of said determining performed in step (g).

36. The method according to claim 29 wherein a visually noisy background is projected on said retina such that at least said first pattern and said second pattern are projected on said retina in the presence of said visually noisy background.

37. The method according to claim 1 wherein said first pattern comprises at least one immobilized component that flashes on and off at least once.

38. The method according to claim 1 wherein said first pattern comprises at least one moving component.

39. The method according to claim 1 wherein step (b) comprises the individual bringing a cursor to said fixation target.

40. The method according to claim 39 wherein step (e) comprises said individual bringing a cursor to the approximate position at which said difference is detected in said perceived image.

41. The method according to claim 40 wherein the movement of said cursor is restricted to a predetermined path at least during part of step (e).

42. The method according to claim 39 wherein the movement of said cursor is restricted to a predetermined path at least during the performing of step (e).

43. The method according to claim 1 wherein step (d) occurs upon receiving from said individual an input signal indicating that the individual's vision is fixated at said fixation target.

44. The method according to claim 1 wherein said number of times in step (f) is in the range of 2 to 400 times.

45. The method according to claim 1 wherein said number of times in step (f) is in the range of 60 to 102 times.

46. The method according to claim 1 wherein a visually noisy background is projected on said retina such that at least said second pattern is projected on said retina in the presence of said visually noisy background.

47. The method according to claim 1 wherein step (c) occurs upon receiving from said individual an input signal indicating that the individual's vision is fixated at said fixation target.

48. The method according to claim 1 further comprising a step of analyzing at least part of said plurality of data to determine one or more of the existence of an eye disease in said individual, the extent of said eye disease, the type of said eye disease, the retinal or choroidal location of said eye disease, and combinations thereof.

49. The method according to claim 1 wherein said eye disease is a retinal or choroidal lesion.

50. The method according to claim 49 wherein said retinal or choroidal lesion is related to age related macular degeneration or diabetes.

51. The method according to claim 1 wherein steps (a) to (e) are repeated 2 to 200 times.

52. The method according to claim 1 wherein steps (a) to (e) are repeated 30 to 100 times.

53. The method according to claim 1 wherein said fixation target, said first pattern and said second pattern are projected directly onto said retina of said individual.

54. The method according to claim 1 wherein the projecting of said fixation target, said first pattern and said second pattern is performed by scanning a beam of light on said retina.

55. The method according to claim 54 wherein said beam of light is selected from a beam of coherent light, a beam of incoherent light, and a laser beam.

56. The method according to claim 55 wherein said laser beam is obtained from a scanning laser ophthalmoscope-like device.

57. The method according to claim 1 wherein said plurality of data comprise one or more data items selected from the group consisting of,
   data representing the position on said retina of said second pattern,
   data representing the orientation of said second pattern,
   data representing the presence of an artificial distortion in said second pattern, and
   data representing the position of said artificial distortion within said second pattern.

58. The method according to claim 1 wherein said plurality of data comprises, for at least one of the repetitions of step (f), data representing the position of said difference within said perceived image.

59. The method according to claim 58 wherein step (g) comprises the step of outputting a positive result indicative of the presence of a retinal or choroidal lesion in the eye of said individual if the positions at which said difference is perceived in two or more perceived images of the second test patterns satisfy a proximity criterion.

60. The method according to claim 59 wherein said proximity criterion comprises,
   obtaining data representing a first position on said retina of a perceived difference from a first projecting of the second pattern;
   obtaining data representing a second position on said retina of a perceived difference from a second projecting of the second pattern at a retinal location different than the location of projecting of said first projecting;
   determining if said second position falls within a criterion area computed from said first position; and
   outputting a positive result if said second position falls within said criterion area, satisfying said proximity criterion, or a negative result if said second position does not fall within said criterion area.

61. The method according to claim 59 wherein said reference pattern is selected from a horizontal segmented straight line comprising a plurality of segments, and a vertical segmented straight line comprising a plurality of segments, and said first and second patterns are selected from a horizontal segmented straight line comprising a plurality of segments, a vertical segmented straight line comprising a plurality of segments, a horizontal segmented line comprising a plurality of segments at least one segment of said plurality of segments is vertically displaced relative to the remaining segments of the horizontal line, a vertical segmented line comprising a plurality of segments at least one segment of said plurality of segments is horizontally displaced relative to the remaining segments of the vertical line.

62. The method according to claim 61 wherein step (g) further comprises the steps of:
obtaining data representing a first position on said retina of a perceived difference from a first projecting of the second pattern;
obtaining data representing a second position on said retina of a perceived difference from a second projecting of the second pattern at a retinal location different than the location of projecting of said first projecting;
determining if said second position falls within a criterion area computed from said first position; and
outputting a positive result if said second position falls within said criterion area, satisfying said proximity criterion, or a negative result if said second position does not fall within said criterion area.

63. The method according to claim 62 wherein the second pattern projected in said first projecting is parallel to the second pattern presented in said second projecting, said criterion area is a rectangle, the center of said rectangle is at said first position of said first projecting.

64. The method according to claim 62 wherein for second pattern pairs in which the second pattern projected in said first projecting is orthogonal to the second pattern presented in said second projecting, said criterion area is different than the criterion area computed for second pattern pairs in which the second pattern projected in said first projecting is parallel to the second pattern projected in said second projecting.

65. The method according to claim 64 wherein the test pattern presented in said first presentation is orthogonal to the test pattern presented in said second presentation, said criterion area is a circle, and said first position is the center of said circle.

66. The method according to claim 65 wherein the radius of said circle is a predetermined radius.

67. The method according to claim 65 wherein said radius is empirically determined.

68. The method according to claim 1 wherein step (f) comprises changing the location, or the orientation or the orientation and the location of projecting of at least one pattern of said first and said second patterns on said retina in at least some of the repetitions of steps (a) to (e) performed in step (f).

69. The method according to claim 68 wherein the projecting of a second pattern in at least one selected area of interest on said retina is repeated a selected number of times to increase the reliability of detecting of said eye disease in said at least one area of interest.

70. The method according to claim 68 wherein said changing comprises randomly or pseudo-randomly changing the location, or the orientation or the orientation and the location of projecting of said at least one pattern on said retina.

71. The method according to claim 68 wherein said determining of step (g) comprises outputting a positive result indicative of the presence of a retinal or choroidal lesion in said eye of said individual if said difference is detected in one or more repetitions of step (e).

72. The method according to claim 68 wherein the changing of the location of projecting of said at least one pattern on said retina comprises changing the retinal location of projecting of said at least one pattern or the orientation of projecting of said at least one pattern until said plurality of data are sufficient for providing a predetermined mapping resolution of a selected portion of the retina of said individual.

73. The method according to claim 72 wherein said predetermined mapping resolution is different for different mapped parts of said selected portion of said retina.

74. The method according to claim 73 wherein said selected portion is the macular area of said retina, and wherein said mapping resolution in the fovea of the macular area is higher than the mapping resolution of the remaining non-foveal regions of said macular area.

75. The method according to claim 1 wherein step (f) is performed such that said second pattern is projected only once on the same retinal location.

76. The method according to claim 1 wherein step (f) is performed such that said second pattern may be projected more than once on the same retinal location.

77. The method according to claim 1 wherein step (f) is performed such that one or more of the projected second patterns may be inclined at an angle relative to other second patterns projected within the same test.

78. The method according to claim 1 wherein step (f) is performed such that the projected second patterns represent a grid mapping said retina.

79. The method according to claim 78 wherein said grid is selected from a grid comprising orthogonal straight lines, a grid comprising non-orthogonal straight lines, a grid comprising a plurality of straight lines intersecting at a common intersection point, and a grid comprising a plurality of straight lines having the same length said lines intersect at a common intersection point which bisects each of said lines into two equal parts.

80. A method for detecting eye disease in an individual, the method comprising the steps of:
fixating the individual's vision at or about a fixation target projected at a first retinal location of the retina of an eye of said individual;
projecting for a selected duration a test pattern at a second retinal location of said eye, to allow the individual to form a perceived image of said test pattern;
receiving from said individual input indicative of a difference in at least one localized part of said perceived image as compared to a predefined reference pattern, if said individual detected said difference;
repeating the steps of fixating, projecting and receiving a number of times while changing in at least some of the repetitions of said step of projecting the location of projecting of said test pattern on said retina, to obtain a plurality of data; and
analyzing said plurality of data to determine whether said individual has an eye disease.

81. The method according to claim 80 wherein said analyzing comprises outputting a positive result indicative of the presence of a retinal or choroidal lesion in said eye of said individual if said individual detected said difference in one or more repetitions of said step of repeating.

82. The method according to claim 80 wherein said analyzing comprises outputting a positive result indicative of the presence of a retinal or choroidal lesion in said eye of said individual if said individual detected said difference in one or more repetitions of said step of receiving.

83. The method according to claim 80 wherein said projecting is performed in response to said fixating.

84. The method according to claim 80 wherein the step of fixating, the step of projecting, the step of receiving, the step of repeating and the step of analyzing are performed in the order recited in claim 80.

85. The method according to claim 80 wherein said first location and said second location partially overlap.

86. The method according to claim 80 wherein said first location does not overlap said second location.

87. The method according to claim 80 wherein said test pattern is selected from said predefined reference pattern and a modified form of said reference pattern.

88. The method according to claim 87 wherein said modified form of said reference pattern is selected from,
   a test pattern in which at least one portion of the test pattern is distorted in comparison with said reference pattern,
   a test pattern in which an optical property of at least one portion of the test pattern is different than the corresponding optical property of the remaining portion of said test pattern,
   a test pattern in which at least one portion of the test pattern is perceivably visually different in comparison with the corresponding portion of said reference pattern,
   a test pattern in which at least one portion of the test pattern is missing in comparison with said reference pattern,
   a test pattern in which at least one portion of the test pattern is blurred in comparison with the remaining portion of said test pattern.

89. The method according to claim 88 wherein said optical property is selected from the group consisting of the color of said part, the hue of said part, and the brightness of said part.

90. The method according to claim 80 wherein the projected test pattern and the predefined reference pattern are substantially identical, and wherein the perceived image and the predefined reference pattern are not identical.

91. The method according to claim 80 wherein the projected test pattern and the predefined reference pattern are not identical.

92. The method according to claim 91 wherein the projected test pattern is similar to an image perceived by an individual having an eye disease when said reference pattern is projected on a diseased part of the retina of said individual having an eye disease.

93. The method according to claim 91 wherein the projected test pattern is configured to be similar to the image perceived by an individual with eye disease when the predefined reference pattern is projected onto a location of the eye having a retinal or choroidal lesion.

94. The method according to claim 91 wherein said reference pattern comprises a plurality of components, said test pattern is obtained by a modification of said reference pattern, and the modification is selected from the group consisting of:
   displacing or moving at least one component of said reference pattern relative to the remaining components of said reference pattern,
   removing or hiding at least one component of said reference pattern,
   blurring at least one component of said reference pattern,
   changing a visually perceivable characteristic of at least one component of said reference pattern, and
   changing an optical property of at least one component of said reference pattern.

95. The method according to claim 80 wherein said reference pattern and said test pattern comprise one or more lines.

96. The method according to claim 95 wherein said reference pattern and said test pattern comprise one or more straight lines.

97. The method according to claim 95, wherein one or more of said lines is a segmented line comprising a plurality of segments.

98. The method according to claim 80 wherein said reference pattern is a segmented straight line comprising a plurality of segments, and said test pattern is selected from the group consisting of,
   a segmented straight line comprising a plurality of segments,
   a segmented line comprising a plurality of segments at least one segment of said plurality of segments is displaced relative to the remaining segments,
   a segmented straight line comprising a plurality of segments at least one segment of said plurality of segments is blurred relative to the remaining segments,
   a segmented straight line comprising a plurality of segments said plurality of segments is shaped and arranged similarly to the plurality of segments of said reference pattern except that one or more of the segments of the reference pattern is missing in said test pattern,
   a segmented straight line comprising a plurality of segments, at least one segment of said plurality of segments has an optical property which is different than the optical property of the remaining segments of said segmented straight line, and
   a segmented straight line comprising a plurality of segments, at least one segment of said plurality of segments has a visually perceivable characteristic which is different than the visually perceivable characteristic of the remaining segments.

99. The method according to claim 80 wherein said selected duration is in the range of about 10 milliseconds to 20 seconds.

100. The method according to claim 80 wherein said selected duration is in the range of about 100-160 milliseconds.

101. The method according to claim 80 wherein said selected duration is long enough to enable said individual to perceive an image of said test pattern and shorter than the duration of a saccade.

102. The method according to claim 80 wherein said difference is selected from
   at least one portion of said perceived image is distorted in comparison with said reference pattern,
   an optical property of at least one portion of said perceived image is different than the corresponding optical property of the remaining portion of said perceived image,
   a visual characteristic of at least one portion of said perceived image is different than the corresponding visual characteristic of the remaining portion of said perceived image,
   at least one portion of said perceived image is missing in comparison with said reference pattern,
   at least one portion of said perceived image is blurred in comparison with the remaining portion of said perceived image, and
   at least one portion of the perceived image of said test pattern is perceived to at least temporarily move with respect to the remaining portion of said perceived image.

103. The method according to claim 80 wherein said plurality of data comprises data representing the approximate location of said difference within said perceived image of said test pattern.

104. The method according to claim 103 wherein the plurality of data analyzed in said step of analyzing comprises data representing the location on said retina at which said test pattern is projected in said step of projecting.

105. The method according to claim 104 wherein said data comprises data representing the orientation on said retina of said test pattern projected in said step of projecting.

106. The method according to claim 80 wherein said step of analyzing comprises the step of outputting a positive result indicative of the presence of a retinal or choroidal lesion in said eye of said individual if said difference is detected in at least one repetition of said step of projecting.

107. The method according to claim 80 wherein said step of analyzing further comprises the steps of:
obtaining data representing a first position on said retina of a perceived difference from a first presentation of a test pattern;
obtaining data representing a second position on said retina of a perceived difference from a second presentation of a test pattern;
determining if said second position falls within a criterion area computed from said first position; and
outputting a positive result if said second position falls within said criterion area, satisfying said proximity criterion, or a negative result if said second position does not fall within said criterion area.

108. The method according to claim 80 wherein said plurality of data comprises for each test pattern projected in said step of projecting one or more data items selected from the group of data items consisting of,
data, received from said individual, the data representing the position or positions at which said difference is detected within said perceived image,
data representing the position on said retina of said test pattern,
data representing the orientation of said test pattern,
data representing the presence of an artificial distortion in said test pattern, and
data representing the position of said artificial distortion within said test pattern.

109. The method according to claim 108 wherein said step of analyzing comprises the step of outputting a positive result indicative of the presence of a retinal or choroidal lesion in said eye of said individual if the positions at which said difference is perceived in two or more test pattern presentations satisfy a proximity criterion.

110. The method according to claim 109 wherein said reference pattern is selected from a horizontal segmented straight line comprising a plurality of segments, and a vertical segmented straight line comprising a plurality of segments, and said test pattern is selected from a horizontal segmented straight line comprising a plurality of segments, a vertical segmented straight line comprising a plurality of segments, a horizontal segmented line comprising a plurality of segments at least one segment of said plurality of segments is vertically displaced relative to the remaining segments of the horizontal line, a vertical segmented line comprising a plurality of segments at least one segment of said plurality of segments is horizontally displaced relative to the remaining segments of the vertical line.

111. The method according to claim 110 wherein said step of analyzing further comprises the steps of:
obtaining data representing a first position on said retina of a perceived difference from a first presentation of a test pattern;
obtaining data representing a second position on said retina of a perceived difference from a second presentation of a test pattern;
determining if said second position falls within a criterion area computed from said first position; and
outputting a positive result if said second position falls within said criterion area, satisfying said proximity criterion, or a negative result if said second position does not fall within said criterion area.

112. The method according to claim 111 wherein the test pattern presented in said first presentation is parallel to the test pattern presented in said second presentation, said criterion area is a rectangle, the center of said rectangle is at said first position of said first projecting.

113. The method according to claim 111 wherein for test pattern pairs in which the test pattern presented in said first presentation is orthogonal to the test pattern presented in said second presentation said criterion area is different than the criterion area computed for test pattern pairs in which the test pattern presented in said first presentation is parallel to the test pattern presented in said second presentation.

114. The method according to claim 113 wherein the test pattern presented in said first presentation is orthogonal to the test pattern presented in said second presentation, said criterion area is a circle, and said first position is the center of said circle.

115. The method according to claim 114 wherein the radius of said circle is a predetermined radius.

116. The method according to claim 114 wherein said radius is empirically determined.

117. The method according to claim 80 wherein the changing of the location of projecting of said test pattern on said retina in said step of projecting comprises randomly or pseudo-randomly changing the location of projecting of said test pattern on said retina.

118. The method according to claim 80 wherein the changing of the location of projecting of said test pattern on said retina in said step of projecting comprises changing the retinal location of projecting of said test pattern until the number and locations of the projected test patterns is sufficient for providing a predetermined mapping resolution of a selected portion of the retina of said individual.

119. The method according to claim 118 wherein said predetermined mapping resolution is different for different mapped parts of said selected portion of said retina.

120. The method according to claim 119 wherein said selected portion is the macular area of said retina, and wherein said mapping resolution in the fovea of the macular area is higher than the mapping resolution of the remaining non-foveal regions of said macular area.

121. The method according to claim 118 wherein the projecting of a test pattern in at least one selected area of interest on said retina is repeated a selected number of times to increase the reliability of detecting of said disease in said at least one area of interest.

122. The method according to claim 80 wherein said step of repeating is performed such that a test pattern is projected only once on the same retinal location.

123. The method according to claim 80 wherein said step of repeating is performed such that a test pattern may be projected more than once on the same retinal location.

124. The method according to claim 80 wherein said step of repeating is performed such that one or more projected test pattern may be inclined at an angle relative to other test patterns projected within the same test.

125. The method according to claim 80 wherein said step of repeating is performed such that the projected test patterns represent a grid mapping said retina.

126. The method according to claim 80 wherein said grid is selected from a grid comprising orthogonal straight lines, a grid comprising non-orthogonal straight lines, a grid comprising a plurality of straight lines intersecting at a common intersection point, and a grid comprising a plurality of straight lines having the same length said lines intersect at a common intersection point which bisects each of said lines into two equal parts.

127. The method according to claim 80 wherein said analyzing comprises determining one or more of the existence of an eye disease in said individual, the extent of said eye disease, the type of said eye disease, the location of said eye disease, and combinations thereof.

128. The method according to claim 80 wherein one or more data items of said plurality of data are transmitted over a communication network to a processor and stored in a storage device.

129. The method according to claim 128 wherein said communication network is a computer network such as local area network, a wide area network, the Internet, an intranet, a LAN, a WAN or a PAN.

130. The method according to claim 128 wherein one or more data items of said plurality of data is transmitted over the communication network in real time.

131. The method according to claim 128 further comprising a step of transmitting over the communication network data representing the times at which the method is performed by the individual and storing the data representing the times in a database.

132. The method according to claim 131 further comprising a step of sending a reminder to the individual to perform the test if the individual fails to perform the test as instructed by a health care provider.

133. The method according to claim 131 further comprising a step of transmitting over the communication network to a health care provider the results of an analysis of said plurality of data.

134. The method according to claim 80 wherein said step of fixating comprises the individual bringing a cursor to said fixation target.

135. The method according to claim 134 wherein said step of receiving comprises said individual bringing a cursor to the approximate position at which said difference is detected in said perceived image.

136. The method according to claim 135 wherein the movement of said cursor is restricted to a predetermined path at least during part of said step of receiving.

137. The method according to claim 80 wherein the step of projecting said test pattern occurs upon receiving from said individual an input signal indicating that the individual's vision is fixated at said fixation target.

138. The method according to claim 80 wherein said number of times of said step of repeating is in the range of 2 to 400 times.

139. The method according to claim 80 wherein said number of times of said step of repeating is in the range of 60 to 102 times.

140. The method according to claim 80 wherein a visually noisy background is projected on said retina such that at least said test pattern is projected on said retina in the presence of said visually noisy background.

141. A method for detecting eye disease in an individual, comprising steps of:
(a) projecting a first pattern at a first location on the retina of an eye of said individual;
(b) fixating the individual's vision on a fixation target in or about said first pattern;
(c) hiding at least a portion of said first pattern;
(d) projecting a second pattern at a second location of said retina to allow the individual to form a perceived image of said second pattern;
(e) if said individual perceived a difference between said second pattern and a predefined reference pattern, receiving from said individual data indicative of said difference;
(f) repeating steps (a) to (e) a number of times such that for at least some of the repetitions of steps (a) to (e), the first pattern of step (a) of the current repetition of steps (a) to (e) is projected at the second location of step (d) of the preceding repetition of steps (a) to (e), and the second pattern of step (d) of the current repetition of steps (a) to (e) is projected at a retinal location different than the second location of step (d) of the preceding repetition of Steps (a) to (e), to obtain a plurality of data; and
(g) analyzing said plurality of data to determine whether said individual has an eye disease.

142. The method according to claim 141 wherein said data comprises the approximate position of said difference within said perceived image.

143. The method according to claim 141 wherein said plurality of data comprises one or more of data representing said second location of said second pattern for at least some of the repetitions of step (d), data representing the orientation of said second pattern for at least some of the repetitions of step (d), data representing the approximate position of said difference within said perceived image for repetitions of step (d) in which a difference is reported by said individual, and combinations thereof.

144. The method according to claim 141 wherein the predefined reference pattern and the second pattern each comprises a plurality of components and wherein said difference is selected from the group consisting of:
a component of said perceived image that is displaced relative to the corresponding component of said reference pattern;
at least one component of the reference pattern that is missing in the perceived image;
at least one component of the perceived image that is blurred in comparison to the remaining components of the perceived image;
at least one component of the reference pattern having an altered optical property in the perceived image; and
at least one component of the perceived image that is visually perceivably different than the remaining components of said perceived image.

145. The method according to claim 141 wherein said second pattern is identical to said first pattern.

146. The method according to claim 141 wherein said second pattern is different from said first pattern.

147. The method according to claim 141 wherein said second pattern is a modified form of said first pattern or of said predefined reference pattern.

148. The method according to claim 141 wherein said second pattern is a modified form of said predefined reference pattern.

149. The method according to claim 141 wherein said projecting is performed by displaying said first pattern and said second pattern on a display device.

150. The method according to claim 141 wherein said projecting is performed by projecting said first pattern and said second pattern directly onto said retina of said individual.

151. The method according to claim 141 wherein said projecting is performed by scanning a beam of light on said retina.

152. The method according to claim 151 wherein said beam of light is selected from a beam of coherent light, a beam of incoherent light and a laser beam.

153. The method according to claim 152 wherein said laser beam is obtained from a scanning laser ophthalmoscope-like device.

154. A method for administering an eye test to a patient, the method comprising:
　presenting within the field of vision of an eye of said patient a fixation target;
　fixating an eye of said patient on said fixation target;
　presenting, for a presentation duration, a test pattern within the field of vision of said eye, to allow said patient to form a perceived image of said test pattern;
　obtaining from said patient input indicative of a difference in at least one localized part of said perceived image as compared to a predefined reference pattern, if said individual detected said difference; and
　repeating the step of fixating, the second step of presenting and the step of obtaining a selected number of times to obtain a plurality of data, wherein for at least some repetitions of the second step of presenting at least one parameter of said test pattern is modified, said at least one parameter is selected from the location of said test pattern relative to said fixation target, the orientation of said test pattern within said field of vision, and the shape or visual appearance of at least a portion of said test pattern.

155. The method according to claim 154 wherein said presenting is performed in response to said fixating.

156. A method for administering an eye test to a patient, the method comprising:
　(a) presenting within the field of vision of an eye of said patient a fixation target and a first pattern;
　(b) fixating an eye of said patient on said fixation target;
　(d) hiding at least a portion of said first pattern;
　(e) presenting a second pattern within the field of vision of said eye, to allow said patient to form a perceived image of said second pattern;
　(f) obtaining from said patient input indicative of a difference in at least one localized part of said perceived image as compared to a predefined reference pattern, if said individual detected said difference; and
　(g) repeating steps (a) to (f) a selected number of times to obtain a plurality of data, wherein for at least some of the repetitions of step (a) to (e) at least one parameter of the first pattern or the second pattern is modified, said at least one parameter is selected from the location of one or more of said first pattern and second pattern in said field of vision, the orientation of said first pattern and said second pattern within said field of vision, and the shape or visual appearance of at least a portion of said second pattern.

157. The method according to claim 156 wherein steps (d) and (e) are performed in response to the fixating of step (b).

158. A method for administering an eye test to a patient, the method comprising the steps of:
　presenting within the field of vision of an eye of said patient a fixation target;
　fixating an eye of said patient on said fixation target;
　presenting, for a presentation duration, a test pattern within the field of vision of said eye, to allow said patient to form a perceived image of said test pattern;
　obtaining from said patient, if said patient detected in said perceived image a deviation of part of said perceived image from the visual appearance of the corresponding part of a predefined reference pattern, a response representing at least the presence of said deviation; and
　repeating the step of fixating, the second step of presenting and the step of obtaining a selected number of times to obtain a plurality of data, wherein for at least some repetitions of the second step of presenting at least one parameter of said test pattern is modified, said at least one parameter is selected from the location of said test pattern relative to said fixation target, the orientation of said test pattern within said field of vision, and the shape or the visually perceivable appearance of at least one portion of said test pattern.

159. The method according to claim 158 wherein at least one parameter of said test pattern is modified to mimic the image perceived by a person having a lesioned retinal or choroidal region when a test pattern similar to said predefined reference pattern is projected on said lesioned region.

160. A method for administering an eye test to a patient, the method comprising the steps of:
　(a) presenting within the field of vision of an eye of said patient a fixation target and a first pattern;
　(b) fixating an eye of said patient on said fixation target;
　(c) presenting a second pattern within the field of vision of said eye, to allow said patient to form a perceived image of said second pattern;
　(d) obtaining from said patient, if said patient detected in said perceived image a deviation of at least one part of said perceived image from the visual appearance of the corresponding part of a predefined reference pattern, a response representing at least the presence of said deviation;
　(e) repeating steps (a) to (d) a selected number of times to obtain a plurality of data, wherein for at least some repetitions of step (c) at least one parameter of said first pattern or said second pattern is modified, said at least one parameter is selected from
　the location of presenting of one or more of said first pattern and second pattern within said field of view,
　the orientation of one or more of said first pattern and second pattern within said field of view, and
　the shape or the visually perceivable appearance of at least one portion of said second pattern.

161. The method according to claim 160 wherein at least one parameter of said second pattern is modified to mimic the image perceived by a person having a lesioned retinal or choroidal region when a pattern similar to said predefined reference pattern is projected on said lesioned region.

162. A method for detecting eye disease in an individual, the method comprising the steps of:
　fixating the individual's vision at or about a fixation target projected at a first retinal location of the retina of an eye of said individual;
　projecting for a selected duration a test pattern at a second retinal location of said eye, to allow the individual to form a perceived image of said test pattern;
　receiving from said individual, if said individual detected one or more differences between said perceived image and a predefined reference pattern, data indicative of the position of said one or more differences within the perceived image of said test pattern;

repeating the steps of fixating, projecting and receiving a number of times while changing the location of projecting of said test pattern on said retina in said step of projecting, to obtain a plurality of data; and analyzing said plurality of data to determine whether said individual has an eye disease.

163. The method according to claim 162 wherein the projecting of said fixation target and said test pattern is performed by a method selected from, projecting said fixation target and said test pattern directly onto the retina of said eye, scanning images of said fixation target and said test pattern onto the retina of said eye using a scanning beam of light, and displaying said fixation target and said test pattern on a display device.

164. The method according to claim 162 wherein said fixating, said projecting, said receiving, said repeating and said analyzing are performed in the order recited in claim 162.

165. A method for detecting eye disease in an individual, the method comprising the steps of:

(a) projecting a first pattern at a first location of the retina of an eye of said individual;

(b) fixating the individual's vision at or about a fixation target projected at or about said first location;

(c) hiding at least a portion of said first pattern;

(d) projecting a second pattern at a second retinal location of said eye, to allow the individual to form a perceived image of said second pattern;

(e) receiving from said individual, if said individual detected one or more differences between said perceived image and a predefined reference pattern, data indicative of the position of said one or more differences within the perceived image of said test pattern;

(f) repeating steps (a) to (e) a number of times while changing the location of projecting of said second pattern on said retina, to obtain a plurality of data; and (g) analyzing said plurality of data to determine whether said individual has an eye disease.

166. The method according to claim 165 wherein the projecting of said fixation target, said first pattern and said second pattern is performed by a method selected from, projecting said fixation target, said first pattern and said second pattern directly onto the retina of said eye, scanning images of said fixation target, said first pattern and said second pattern onto the retina of said eye using a scanning beam of light, and displaying said fixation target, said first pattern and said second pattern on a display device.

167. The method according to claim 165 wherein steps (a) to (g) are performed in the order recited in claim 165.

168. A method for performing an eye test, the method comprising:

projecting a test pattern at a position on a retina of an individual for a presentation duration while the individual's vision is fixated on a fixation target projected on said retina to allow said individual to form a perceived image of the test pattern wherein at least one parameter of said test pattern is modified to mimic an image perceived by a person having a lesioned retinal or choroidal region when a predefined reference pattern is projected on said lesioned region; and if said perceived image includes at least one localized difference when compared to said predefined reference pattern, receiving from said patient input indicating the position within said perceived image of said at least one difference.

169. The method according to claim 168 further including repeating said projecting and said receiving a number of times to obtain a plurality of data, wherein for at least some repetitions of said projecting one or more of the location of said test pattern relative to said fixation target and the orientation of projecting of said test pattern on said retina is modified.

170. A method for performing an eye test, the method comprises:

projecting for a first duration a first test pattern at a first position of a retina of an individual to allow said individual to form a first perceived image of said first test pattern;

projecting for a second duration a second test pattern at a second position of said retina while the individual's vision is fixated on a fixation target projected in or near said first test pattern, to allow said patient to perceive a second perceived image of said second test pattern, wherein at least one parameter of said second pattern is modified to mimic an image perceived by a person having a lesioned retinal or choroidal region when a predefined reference pattern is projected on said lesioned region; and receiving from said patient an input if said second perceived image included at least one localized difference when compared to said first perceived image or to said predefined reference pattern, said input indicates at least the position within said second perceived image at which said at least one difference is detected.

171. The method according to claim 170 further including repeating said first projecting, said second projecting and said receiving a number of times to obtain a plurality of data, wherein for at least some repetitions of said projecting one or more of the location of said first pattern, the location of said second pattern, and the orientation of projecting of said first pattern and said second pattern on said retina is modified.

172. A system for performing an eye test in an individual, the system comprising:

means for displaying patterns to the individual;

means for fixating the individual's vision on a point in a pattern displayed on said means for displaying and for hiding at least a portion of said pattern after the individual's vision has been fixated on said point;

means for selecting a portion of a pattern displayed on said means for displaying; and processing means operatively coupled to said means for displaying, and said means for selecting, said processing means is configured to perform the steps of, displaying to the individual a first pattern at a first location on said means for displaying, determining when the individual's vision is fixated on a point within said first pattern or near said first pattern, hiding at least a portion of said first pattern upon the individual fixating his vision on said point of said first pattern, displaying a second pattern to the individual at a second location on said means for displaying to allow the individual to form a perceived image of said second pattern, and receiving from said individual input indicative of a difference in at least one localized part of said perceived image as compared to a predefined reference pattern, if said individual detected said difference.

173. The system according to claim 172 further comprising means for storing data representing said difference.

174. The system according to claim 172 wherein at least one of said means for displaying, means for selecting and means for fixating comprises one or more devices selected from a touch sensitive display device, a pointing device, a light pen, joystick, a mouse, a keyboard, a computer input device, and combinations thereof.

175. The system according to claim 172 wherein said means for displaying said means for fixating and said means for selecting comprise a touch sensitive display device.

176. The system according to claim 172 wherein said means for fixating comprises a device for moving a cursor or a pattern displayed on said means for displaying.

177. The system according to claim 176 wherein said means for fixating is selected from a pointing device, a computer input device, a computer mouse, a keyboard, a joystick, a light pen and a touch sensitive screen.

178. The system according to claim 172 wherein said means for selecting comprises a pointing device for operatively moving a cursor displayed by said means for displaying.

179. The system according to claim 172 wherein said processing means comprises at least one processing device selected from a processor, a microprocessor, a computer, a computing device, a personal computer, a laptop computer, a controller, a remote processor or computer, a server, a remote server, a networked computer, and combinations thereof.

180. The system according to claim 172 wherein said means for displaying is selected from a display device, a beam scanning device, and a laser scanning ophthalmoscope-like device.

181. The system according to claim 172 wherein at least one of said means for fixating and means for selecting comprises a device selected from a pointing device, a computer input device, a keyboard, a mouse, a graphic tablet, a light pen, a touch sensitive screen, and combinations thereof.

182. The system according to claim 172 wherein said processing means are configured to repeat the first step of displaying, the step of determining the step of hiding, the second step of displaying and the step of receiving a number of times to obtain a plurality of data, and to process said plurality of data for detecting an eye disease in said individual.

183. The system according to claim 172 wherein said processing means are configured to repeat the first step of displaying, the step of determining, the step of hiding, the second step of displaying and the step of receiving a number of times to obtain a plurality of data, and wherein said system comprises communication means for communicating said plurality of data for processing outside of said system.

184. The system according to claim 172 wherein said system also comprises communication means for communicating with one or more devices outside of said system.

185. The system according to claim 172 wherein said second pattern is selected from said predefined reference pattern and a modified form of said reference pattern.

186. The system according to claim 185 wherein said modified form of said reference pattern is selected from,
a test pattern in which at least one portion of the test pattern is distorted in comparison with said reference pattern,
a test pattern in which an optical property of at least one portion of the test pattern is different than the corresponding optical property of the remaining portion of said test pattern,
a test pattern in which at least one portion of the test pattern is perceivably visually different in comparison with the corresponding portion of said reference pattern,
a test pattern in which at least one portion of the test pattern is missing in comparison with said reference pattern, and
a test pattern in which at least one portion of the test pattern is blurred in comparison with the remaining portion of said test pattern.

187. A system for performing an eye test in an individual, comprising:
a displaying device configured for displaying to said individual patterns on a surface;
a device for fixating the individual's vision on a point in a pattern displayed on said surface and for hiding at least a portion of said pattern after the individual's vision has been fixated on the point;
a device for selecting a portion of a pattern displayed on said surface; and
a processing unit configured to carry out the steps of,
displaying to the individual a first pattern at a first location on a surface,
determining when the individual's vision is fixated on a point within said first pattern or near said first pattern,
hiding at least a portion of the first pattern upon the individual fixating his vision on a point in the first pattern,
displaying a second pattern to the individual at a second location on the surface to allow said individual to form a perceived image, and
receiving from said individual input indicative of a difference in at least one localized part of said perceived image as compared to a predefined reference pattern, if said individual detected said difference.

188. The system according to claim 187 further comprising a storage unit for storing data representing said difference.

189. The system according to claim 187 wherein said surface is part of a displaying device operatively coupled to said device for fixating.

190. The system according to claim 187 wherein the device for fixating the individual's vision on a point of the surface comprises a device for moving a cursor or a pattern displayed by said displaying device.

191. The system according to claim 190 wherein said device for fixating is selected from a pointing device, a computer input device, a computer mouse, a keyboard, a joystick, a light pen and a touch sensitive screen.

192. The system according to claim 187 wherein the device for selecting a portion of a pattern comprises a pointing device for operatively moving a cursor on said surface.

193. The system according to claim 187 wherein at least one of said displaying device, said device for selecting and said device for fixating comprises one or more devices selected from a touch sensitive display device, a pointing device, a light pen, joystick, a mouse, a keyboard, a computer input device, and combinations thereof.

194. The system according to claim 187 wherein said processing unit is configured to repeat the first step of displaying, the step of determining, the step of hiding, the second step of displaying and the step of receiving a number of times to obtain a plurality of data, and to process said plurality of data for detecting an eye disease in said individual.

195. The system according to claim 187 wherein said processing unit is configured to repeat the first step of displaying, the step of determining, the step of hiding, the second step of displaying and the step of receiving a number of times to obtain a plurality of data, and wherein said system comprises communication means for communicating said plurality of data for processing outside of said system.

196. The system according to claim 187 wherein said system also comprises communication means for communicating with one or more devices outside of said system.

197. The system according to claim 187 wherein said second pattern of said step of projecting is selected from said predefined reference pattern and a modified form of said reference pattern.

198. The system according to claim 197 wherein said modified form of said reference pattern is selected from,
- a test pattern in which at least one portion of the test pattern is distorted in comparison with said reference pattern,
- a test pattern in which an optical property of at least one portion of the test pattern is different than the corresponding optical property of the remaining portion of said test pattern,
- a test pattern in which at least one portion of the test pattern is perceivably visually different in comparison with the corresponding portion of said reference pattern,
- a test pattern in which at least one portion of the test pattern is missing in comparison with said reference pattern, and
- a test pattern in which at least one portion of the test pattern is blurred in comparison with the remaining portion of said test pattern.

199. A system for detecting eye disease in an individual, the system comprising:
- means for projecting patterns on the retina of an eye of said individual;
- means for fixating the individual's vision on a fixation target projected on said retina;
- means for providing input representative of the position of a selected region of said retina at which a difference is observed by said individual between a perceived image of one of said patterns and a predetermined reference pattern; and
- processing means operatively coupled to said means for projecting, said means for fixating, and said means for providing input, said processing means is configured to perform the steps of,
- projecting a first pattern at a first location on said retina,
- determining when the individual's vision is fixated on said fixation target,
- hiding at least a portion of said first pattern after the individual's vision is fixated on said fixation target,
- projecting a second pattern at a second location on said retina to allow said individual to form a perceived image of said second pattern, and
- receiving from said individual input indicative of a difference in at least one localized part of said perceived image as compared to a predefined reference pattern, if said individual detected said difference.

200. The system according to claim 199 further comprising means for storing data indicative of said difference.

201. The system according to claim 199 wherein said processing means comprises at least one processing unit selected from a processor, a microprocessor, a computer, a personal computer, a laptop computer, a controller, a remote processor, a remote computer, a server, a remote server, a networked computer, and combinations thereof.

202. The system according to claim 199 wherein said means for projecting is selected from a display device, a beam scanning device, and a laser scanning ophthalmoscope-like device.

203. The system according to claim 199 wherein at least one of said means for fixating and means for providing input comprises a device selected from the group consisting of a pointing device, a computer input device, a keyboard, a mouse, a light pen, a touch sensitive display device, and combinations thereof.

204. The system according to claim 199 wherein said means for projecting patterns is configured for projecting test patterns and fixation targets on said retina.

205. The system according to claim 199 wherein at least one of said means for projecting, means for providing input and means for fixating comprises one or more devices selected from a touch sensitive display device, a pointing device, a light pen, joystick, a mouse, a keyboard, a computer input device, and combinations thereof.

206. The system according to claim 199 wherein said means for projecting said means for fixating and said means for providing input comprise a touch sensitive display device.

207. The system according to claim 199 wherein said means for fixating comprises a device for moving a cursor or a pattern projected by said means for projecting.

208. The system according to claim 207 wherein said means for fixating is selected from a pointing device, a computer input device, a computer mouse, a keyboard, a joystick, a light pen and a touch sensitive screen.

209. The system according to claim 199 wherein said means for providing input comprises a pointing device for operatively moving a cursor or a pattern displayed by said means for projecting.

210. The system according to claim 199 wherein said processing means are configured to repeat the first step of projecting, the step of hiding, the second step of projecting and the step of receiving a number of times to obtain a plurality of data, and to process said plurality of data for detecting said eye disease.

211. The system according to claim 199 wherein said processing means are configured to repeat the first step of projecting, the step of hiding, the second step of projecting and the step of receiving a number of times to obtain a plurality of data, and wherein said system comprises communication means for communicating said plurality of data for processing outside of said system.

212. The system according to claim 199 wherein said system also comprises communication means for communicating with one or more devices outside of said system.

213. The system according to claim 199 wherein said second pattern is selected from said predefined reference pattern and a modified form of said reference pattern.

214. The system according to claim 213 wherein said modified form of said reference pattern is selected from,
- a test pattern in which at least one portion of the test pattern is distorted in comparison with said reference pattern, a test pattern in which an optical property of at least one portion of the test pattern is different than the corresponding optical property of the remaining portion of said test pattern, a test pattern in which at least one portion of the test pattern is perceivably visually different in comparison with the corresponding portion of said reference pattern, a test pattern in which at least one portion of the test pattern is missing in comparison with said reference pattern, and a test pattern in which at least one portion of the test pattern is blurred in comparison with the remaining portion of said test pattern.

215. A system for detecting eye disease in an individual, the system comprising:

means for projecting test patterns and fixation targets on the retina of an eye of said individual;

means for fixating the individual's vision on a fixation target projected on said retina;

means for providing input representative of the position on said retina at which a difference is observed by said individual between a perceived image of one of said patterns and a predetermined reference pattern; and processing means operatively coupled to said means for projecting, said means for fixating, and said means for providing input, said processing means is configured to perform the steps of fixating the individual's vision at or about a fixation target projected at a first location of said retina, projecting for a selected duration a test pattern at a second location of said retina, to allow said individual to form a perceived image of said test pattern, receiving from said individual input indicative of a difference in at least one localized part of the perceived image of said step of projecting as compared to a predefined reference pattern, if said individual detected said difference, repeating the steps of fixating, projecting and receiving a number of times while changing the location of projecting of said test pattern on said retina in said step of projecting, to obtain a plurality of data, and analyzing said plurality of data to determine whether said individual has an eye disease.

216. The system according to claim 215 further comprising means for storing said plurality of data.

217. The system according to claim 215 wherein said processing means comprises at least one processing unit selected from a processor, a microprocessor, a computer, a personal computer, a minicomputer, a laptop computer, a controller, a remote processor or computer, a server, a remote server, a networked computer, and combinations thereof.

218. The system according to claim 215 wherein said means for projecting is selected from a display device, a beam scanning device, and a laser scanning ophthalmoscope-like device.

219. The system according to claim 215 wherein at least one of said means for fixating and means for providing input comprises a device selected from the group consisting of a pointing device, a computer input device, a keyboard, a mouse, a graphic tablet, a light pen, a touch sensitive screen, and combinations thereof.

220. The system according to claim 215 wherein said means for projecting patterns is configured for projecting test patterns and fixation targets on said retina.

221. The system according to claim 215 wherein said system also comprises communication means for communicating with one or more devices outside of said system.

222. The system according to claim 215 wherein said test pattern of said step of projecting is selected from said predefined reference pattern and a modified form of said reference pattern.

223. The system according to claim 222 wherein said modified form of said reference pattern is selected from, a test pattern in which at least one portion of the test pattern is distorted in comparison with said reference pattern, a test pattern in which an optical property of at least one portion of the test pattern is different than the corresponding optical property of the remaining portion of said test pattern, a test pattern in which at least one portion of the test pattern is perceivably visually different in comparison with the corresponding portion of said reference pattern, a test pattern in which at least one portion of the test pattern is missing in comparison with said reference pattern, and a test pattern in which at least one portion of the test pattern is blurred in comparison with the remaining portion of said test pattern.

224. A system for detecting eye disease in an individual, the system comprising:

a projecting unit for projecting test patterns and fixation targets on the retina of an eye of said individual;

at least one input device for providing input representing a difference observed by said individual between a perceived image of one of said test patterns and a predetermined reference pattern; and at least one processing unit operatively coupled to said projecting unit and said at least one input device, said at least one processing unit is configured to perform the steps of, fixating the individual's vision at or about a fixation target projected at a first location of said retina, projecting for a selected duration a test pattern at a second location of said retina, to allow said individual to form a perceived image of said test pattern, receiving from said individual input indicative of a difference in at least one localized part of the perceived image of said step of projecting as compared to a predefined reference pattern, if said individual detected said difference, repeating the steps of fixating, projecting and receiving a number of times while changing the location of projecting of said test pattern on said retina in said step of projecting, to obtain a plurality of said data, and analyzing said plurality of data to determine whether said individual has an eye disease.

225. The system according to claim 224 further comprising a storage device for storing said plurality of data.

226. The system according to claim 224 wherein said data is selected from, the presence of said difference within said perceived image, the approximate position within said perceived image of said difference, the position of said test pattern relative to said fixation target, the orientation of said test pattern on said retina, the presence of a distortion in said test pattern, the position of said distortion within said test pattern, the presence in said test pattern of a visually perceivable difference between part of said test pattern and said predefined reference pattern, the position of said part within said test pattern, and combinations thereof.

227. The system according to claim 224 wherein said processing unit is selected from a processor, a microprocessor, a computer, a personal computer, a laptop computer, a controller, a remote processor or computer, a server, a remote server, a networked computer, and combinations thereof.

228. The system according to claim 224 wherein said projecting unit is selected from a display device, a beam scanning device, and a laser scanning ophthalmoscope-like device.

229. The system according to claim 228 wherein said display device comprises a touch sensitive display device.

230. The system according to claim 224 wherein said at least one input device comprises a device selected from the group consisting of a pointing device, a computer input device, a keyboard, a mouse, a light pen, a touch sensitive display device, and combinations thereof.

231. The system according to claim 224 wherein at least one of said projecting unit and said input device comprises one or more devices selected from a touch sensitive display device, a pointing device, a light pen, joystick, a mouse, a keyboard, a computer input device, and combinations thereof.

232. The system according to claim 224 wherein said system also comprises communication means for communicating with one or more devices outside of said system.

233. The system according to claim 224 wherein said test pattern of said step of projecting is selected from said predefined reference pattern and a modified form of said reference pattern.

234. The system according to claim 233 wherein said modified form of said reference pattern is selected from,
- a test pattern in which at least one portion of the test pattern is distorted in comparison with said reference pattern,
- a test pattern in which an optical property of at least one portion of the test pattern is different than the corresponding optical property of the remaining portion of said test pattern,
- a test pattern in which at least one portion of the test pattern is perceivably visually different in comparison with the corresponding portion of said reference pattern,
- a test pattern in which at least one portion of the test pattern is missing in comparison with said reference pattern, and
- a test pattern in which at least one portion of the test pattern is blurred in comparison with the remaining portion of said test pattern.

235. A system for performing an eye test in an individual, the system comprising:
- a projecting unit for projecting test patterns and fixation targets on the retina of an eye of said individual;
- at least one input device for providing input representing a difference observed by said individual between a perceived image of one of said test patterns and a predetermined reference pattern; and
- at least one processing unit operatively coupled to said projecting unit and said at least one input device, said at least one processing unit is configured to perform the steps of,
    - fixating the individual's vision at or about a fixation target projected at a first location of said retina,
    - projecting for a selected duration a test pattern at a second location of said retina, to allow said individual to form a perceived image of said test pattern, and
    - receiving from said individual input indicative of a difference in at least one localized part of the perceived image of said step of projecting as compared to a predefined reference pattern, if said individual detected said difference.

236. The system according to claim 235 wherein said at least one processing unit is configured to repeat the step of fixating, the step of projecting, and the step of receiving a number of times to obtain a plurality of data, and to process said plurality of data for detecting said eye disease.

237. The system according to claim 235 wherein said at least one processing unit is configured to repeat the step of fixating, the step of projecting, and the step of receiving a number of times to obtain a plurality of data, and wherein said system comprises communication means for communicating said plurality of data for processing outside of said system.

238. The system according to claim 235 wherein said test pattern of said step of projecting is selected from said predefined reference pattern and a modified form of said reference pattern.

239. The system according to claim 238 wherein said modified form of said reference pattern is selected from,
- a test pattern in which at least one portion of the test pattern is distorted in comparison with said reference pattern,
- a test pattern in which an optical property of at least one portion of the test pattern is different than the corresponding optical property of the remaining portion of said test pattern,
- a test pattern in which at least one portion of the test pattern is perceivably visually different in comparison with the corresponding portion of said reference pattern,
- a test pattern in which at least one portion of the test pattern is missing in comparison with said reference pattern, and
- a test pattern in which at least one portion of the test pattern is blurred in comparison with the remaining portion of said test pattern.

240. A system for performing an eye test in an individual, the system comprising:
- means for projecting test patterns and fixation targets on the retina of an eye of said individual;
- means for fixating the individual's vision on a fixation target projected on said retina;
- means for providing input representative of the position on said retina at which a difference is observed by said individual between a perceived image of one of said patterns and a predetermined reference pattern; and
- processing means operatively coupled to said means for projecting, said means for fixating, and said means for providing input, said processing means is configured to perform the steps of,
    - fixating the individual's vision at or about a fixation target projected at a first location of said retina,
    - projecting for a selected duration a test pattern at a second location of said retina, to allow said individual to form a perceived image of said test pattern, and
    - receiving from said individual input indicative of a difference in at least one localized part of the perceived image of said step of projecting as compared to a predefined reference pattern, if said individual detected said difference.

241. The system according to claim 240 wherein said processing means is configured to repeat the step of fixating, the step of projecting, and the step of receiving a number of times to obtain a plurality of data, and to process said plurality of data for detecting an eye disease in said individual.

242. The system according to claim 240 wherein said processing means is configured to repeat the step of fixating, the step of projecting, and the step of receiving a number of times to obtain a plurality of data, and wherein said system comprises communication means for communicating said plurality of data for processing outside of said system.

243. The system according to claim 240 wherein said test pattern of said step of projecting is selected from said predefined reference pattern and a modified form of said reference pattern.

244. The system according to claim 243 wherein said modified form of said reference pattern is selected from,
- a test pattern in which at least one portion of the test pattern is distorted in comparison with said reference pattern,
- a test pattern in which an optical property of at least one portion of the test pattern is different than the corresponding optical property of the remaining portion of said test pattern,
- a test pattern in which at least one portion of the test pattern is perceivably visually different in comparison with the corresponding portion of said reference pattern,
- a test pattern in which at least one portion of the test pattern is missing in comparison with said reference pattern, and
- a test pattern in which at least one portion of the test pattern is blurred in comparison with the remaining portion of said test pattern.

245. A program storage device readable by machine, tangibly embodying a program of instructions executable by the machine to perform method steps for detecting eye disease in an individual, comprising the steps of:
(a) projecting a first pattern on a first location on the retina of an eye of said individual;
(b) fixating the individual's vision on a fixation target projected on said retina at or about said first location;
(c) hiding at least a portion of said first pattern;
(d) projecting a second pattern on a second location of said retina to allow the individual to form a perceived image of said second pattern;
(e) receiving from said individual input indicative of a difference in at least one localized part of said perceived image as compared to a predefined reference pattern, if said individual detected said difference;
(f) repeating steps (a) to (e) a number of times to obtain a plurality of data; and
(g) determining whether the individual has an eye disease based on said plurality of data.

246. A computer program product comprising a computer useable medium having computer readable program code embodied therein for performing an eye test in an individual, the computer program product comprising:
computer readable program code for causing a computer or a projecting device operatively coupled to said computer to project a first pattern on a first location on the retina of an eye of said individual;
computer readable program code for causing the computer to determine when the individual's vision is fixated on a fixation target projected on said retina at or about said first location and for hiding at least a portion of the first pattern when the individual's vision is fixated on said fixation target;
computer readable program code for causing the computer to project a second pattern at a second location of said retina to allow the individual to form a perceived image of said second pattern; and
computer readable program code for causing the computer to receive from said individual input indicative of a difference in at least one localized part of said perceived image as compared to a predefined reference pattern, if said individual detected said difference.

247. The computer program product according to claim 246 wherein the computer readable program code further comprises computer readable program code for causing the computer to repeat the projecting of the first pattern, the determining when the individual's vision is fixated, the hiding of at least a portion of the first pattern, the projecting of the second pattern, and the receiving of said input from said individual a number of times to obtain a plurality of data.

248. The computer program product according to claim 47 wherein the computer readable program code further comprises computer readable program code for causing the computer to determine whether the individual has an eye disease based on said plurality of data.

249. The computer program product according to claim 47 wherein the computer readable program code further comprises computer readable program code for causing the computer to communicate said plurality of data to a device external to said computer for processing said plurality of data to detect eye disease in said individual.

250. A program storage device readable by machine, tangibly embodying a program of instructions executable by the machine to perform method steps for detecting eye disease in an individual, comprising the steps of:
fixating the individual's vision at or about a fixation target projected at a first retinal location of the retina of an eye of said individual;
projecting for a selected duration a test pattern at a second retinal location of said eye, to allow the individual to form a perceived image of said test pattern;
receiving from said individual input indicative of a difference in at least one localized part of said perceived image as compared to a predefined reference pattern, if said individual detected said difference;
repeating the steps of fixating, projecting and receiving a number of times while changing in at least some of the repetitions of said step of projecting the location of projecting of said test pattern on said retina, to obtain a plurality of data; and
analyzing said plurality of data to determine whether said individual has an eye disease.

251. A computer program product comprising a computer useable medium having computer readable program code embodied therein for performing an eye test in an individual, the computer program product comprising:
computer readable program code for causing a computer or a projecting device operatively coupled to said computer to project a fixation target at a first retinal position of an eye of said individual;
computer readable program code for causing the computer to determine when the individual's vision is fixated at or about said fixation target, and for projecting for a selected duration, when the individual's vision is fixated on said fixation target, a test pattern at a second retinal position of said eye, to allow the individual to form a perceived image of said test pattern; and computer readable program code for causing the computer to receive from said individual input indicative of a difference in at least one localized part of said perceived image as compared to a predefined reference pattern, if said individual detected said difference.

252. The computer program product according to claim 251 wherein the computer readable program code further comprises computer readable program code for causing the computer to repeat the projecting of the fixation target, the determining when the individual's vision is fixated on the fixation target, the projecting of the test pattern, and the receiving of input from said individual a number of times while changing the location of projecting of said test pattern on said retina, to obtain a plurality of data.

253. The computer program product according to claim 252 wherein the computer readable program code further comprises computer readable program code for causing the computer to determine whether the individual has an eye disease based on said plurality of data.

254. The computer program product according to claim 252 wherein the computer readable program code further comprises computer readable program code for causing the computer to communicate said plurality of data to a device external to said computer for processing said plurality of data to detect an eye disease in said individual.

* * * * *